(12) United States Patent
Stephan

(10) Patent No.: US 10,737,110 B2
(45) Date of Patent: Aug. 11, 2020

(54) LIGHT THERAPY APPARATUS

(71) Applicant: John Stephan, Troy, MI (US)

(72) Inventor: John Stephan, Troy, MI (US)

( * ) Notice: Subject to any disclaimer, the term of this patent is extended or adjusted under 35 U.S.C. 154(b) by 219 days.

(21) Appl. No.: 15/632,601

(22) Filed: Jun. 26, 2017

(65) Prior Publication Data

US 2017/0291040 A1 Oct. 12, 2017

Related U.S. Application Data

(63) Continuation of application No. 13/673,486, filed on Nov. 9, 2012, now Pat. No. 9,687,669.

(Continued)

(51) Int. Cl.
*A61N 1/36* (2006.01)
*A61F 5/01* (2006.01)
(Continued)

(52) U.S. Cl.
CPC .......... *A61N 5/0616* (2013.01); *A61F 5/0106* (2013.01); *A61F 5/0111* (2013.01);
(Continued)

(58) Field of Classification Search
CPC ......... A61B 18/20; A61B 1/041; A61B 1/043; A61B 5/0071; A61B 5/0075;
(Continued)

(56) References Cited

U.S. PATENT DOCUMENTS 4,118,100 A 10/1978 Goell et al.
4,234,907 A 11/1980 Daniel
(Continued)

FOREIGN PATENT DOCUMENTS

CA 2123745 † 11/1994
CN 1180574 A 5/1998
(Continued)

OTHER PUBLICATIONS

User'S Manual, SAS-XNIB Diode Laser Therapy Apparatus, Zheng An (Beijing) Medical Equipment Co. Ltd., Beijing 2008, cover and pp. 1-20.
(Continued)

*Primary Examiner* — Kim M Lewis
(74) *Attorney, Agent, or Firm* — Young Basile Hanlon & MacFarlane, P.C.

(57) ABSTRACT

A light therapy apparatus is described that includes a housing, a laser mounted in the interior of the housing, and a control circuit that controls the laser according to a control program. The housing includes an opening extending through a first surface of the housing from an interior of the housing. The first surface is perpendicular to the bottom of the housing. The laser is mounted in the interior of the housing so as to output laser light in a direction perpendicular to the bottom of the housing, and the housing and the laser are arranged so that eyes of a user are shielded from direct contact with the laser light output by the laser by the laser light output from the laser being indirectly output through the opening.

20 Claims, 13 Drawing Sheets

Related U.S. Application Data

(60) Provisional application No. 61/640,051, filed on Apr. 30, 2012, provisional application No. 61/557,604, filed on Nov. 9, 2011.

(51) Int. Cl.
  *A61N 5/06* (2006.01)
  *A61M 1/00* (2006.01)
  *A61F 13/00* (2006.01)
  *A61F 13/06* (2006.01)
  *A61F 13/08* (2006.01)
  *A61F 13/10* (2006.01)
  *A61F 13/12* (2006.01)
  *A61F 13/14* (2006.01)
  *A61N 5/067* (2006.01)

(52) U.S. Cl.
  CPC ...... *A61F 5/0118* (2013.01); *A61F 13/00051* (2013.01); *A61F 13/06* (2013.01); *A61F 13/066* (2013.01); *A61F 13/08* (2013.01); *A61F 13/107* (2013.01); *A61F 13/12* (2013.01); *A61F 13/14* (2013.01); *A61M 1/0023* (2013.01); *A61N 5/06* (2013.01); *A61M 1/0088* (2013.01); *A61M 2205/051* (2013.01); *A61N 2005/063* (2013.01); *A61N 2005/067* (2013.01); *A61N 2005/0626* (2013.01); *A61N 2005/0645* (2013.01); *A61N 2005/0659* (2013.01); *A61N 2005/0661* (2013.01); *A61N 2005/0663* (2013.01)

(58) Field of Classification Search
  CPC ... A61B 5/0084; A61B 5/02007; A61B 5/412; A61B 5/418; A61B 5/7267; A61B 8/12; A61B 8/56; A61B 17/00491; A61B 18/14; A61B 18/18; A61B 1/3137; A61B 2017/00106; A61B 2018/1807; A61B 2034/302; A61B 2090/378; A61B 34/30; A61B 34/72; A61B 5/0095; A61B 5/0205; A61B 5/0215; A61B 5/026; A61B 5/0295; A61B 5/053; A61B 5/061; A61B 5/14539; A61B 5/14546; A61B 5/417; A61B 5/6862; A61B 5/6876; A61B 2018/2025; A61B 2018/2261
  USPC .................................................. 602/2; 607/91
  See application file for complete search history.

(56) References Cited

U.S. PATENT DOCUMENTS

| | | | |
|---|---|---|---|
| 4,907,132 A | 3/1990 | Parker | |
| 5,005,108 A | 4/1991 | Pristash et al. | |
| 5,042,900 A | 8/1991 | Parker | |
| 5,092,793 A | 3/1992 | Stephan | |
| 5,136,480 A | 8/1992 | Pristash et al. | |
| 5,339,223 A | 8/1994 | Kremenchugsky et al. | |
| 5,400,425 A | 3/1995 | Nicholas et al. | |
| 5,424,922 A | 6/1995 | Wise | |
| 5,616,140 A | 4/1997 | Prescott | |
| 5,989,245 A | 11/1999 | Prescott | |
| 5,997,569 A | 12/1999 | Chen et al. | |
| 6,156,028 A | 12/2000 | Prescott | |
| 6,165,205 A | 12/2000 | Neuberger | |
| 6,201,915 B1 | 3/2001 | Rizkin et al. | |
| 6,210,425 B1 | 4/2001 | Chen | |
| 6,238,426 B1 | 5/2001 | Chen | |
| 6,290,713 B1 | 9/2001 | Russell | |
| 6,306,160 B1 | 10/2001 | Nidetzky | |
| 6,312,451 B1 | 11/2001 | Streeter | |
| 6,353,763 B1 | 3/2002 | George et al. | |
| 6,454,789 B1 | 9/2002 | Chen et al. | |
| 6,454,791 B1 | 9/2002 | Prescott | |
| 6,494,900 B1 | 12/2002 | Salansky et al. | |
| 6,733,187 B2 | 5/2004 | Page et al. | |
| 6,848,822 B2 | 2/2005 | Ballen et al. | |
| 6,872,220 B2 | 3/2005 | Williams et al. | |
| 6,874,925 B2 | 4/2005 | Page et al. | |
| 6,986,782 B2 | 1/2006 | Chen et al. | |
| 7,100,615 B1 | 9/2006 | Kert | |
| 7,118,563 B2 | 10/2006 | Weckwerth et al. | |
| 7,137,416 B2 | 11/2006 | Brochier et al. | |
| 7,147,653 B2 | 12/2006 | Williams et al. | |
| 7,234,853 B2 | 6/2007 | Givoletti | |
| 7,305,163 B2 | 12/2007 | Williams | |
| 7,331,983 B2 | 2/2008 | Neuberger | |
| 7,374,569 B2 | 5/2008 | Whatcott et al. | |
| 7,479,664 B2 | 1/2009 | Williams | |
| 7,686,839 B2 | 3/2010 | Parker | |
| 7,842,075 B2 | 11/2010 | Kahn et al. | |
| 7,970,624 B2 | 6/2011 | Anderson et al. | |
| 8,109,981 B2 | 2/2012 | Gertner et al. | |
| 8,136,531 B2 | 3/2012 | Chariff | |
| 8,192,473 B2 | 6/2012 | Tucker et al. | |
| 8,286,639 B2 | 10/2012 | Seckel | |
| 8,308,784 B2 | 11/2012 | Streeter et al. | |
| 8,351,750 B2 | 1/2013 | Fine et al. | |
| 8,492,448 B2 | 7/2013 | Dewa et al. | |
| 8,535,361 B2 | 9/2013 | Lim et al. | |
| 8,585,707 B2 | 11/2013 | Rogers | |
| 8,652,061 B2 | 2/2014 | Yu et al. | |
| 8,702,291 B2 | 4/2014 | Stephan | |
| 8,724,942 B2 | 5/2014 | Logunov et al. | |
| 8,760,295 B2 | 6/2014 | Forster | |
| 8,778,002 B2 | 7/2014 | Moy | |
| 8,805,141 B2 | 8/2014 | Fewkes et al. | |
| 8,858,477 B2 | 10/2014 | Pylyp | |
| 8,864,362 B2 | 10/2014 | Sherman et al. | |
| 8,912,142 B2 | 12/2014 | Sprecher et al. | |
| 8,936,630 B2 | 1/2015 | Denison et al. | |
| 8,945,196 B2 | 2/2015 | Huttemann et al. | |
| 8,974,486 B2 | 3/2015 | Kotler | |
| 9,056,198 B2 | 6/2015 | Gerlitz et al. | |
| 9,067,061 B2 | 6/2015 | Samuel et al. | |
| 9,144,690 B2 | 9/2015 | McDaniel | |
| 9,160,132 B2 | 10/2015 | Takada et al. | |
| 9,579,521 B2 | 2/2017 | Ferraz Rigo et al. | |
| 2002/0198576 A1 | 12/2002 | Chen et al. | |
| 2003/0032900 A1 | 2/2003 | Ella | |
| 2004/0073278 A1 | 4/2004 | Pachys | |
| 2004/0077977 A1 | 4/2004 | Ella et al. | |
| 2004/0167500 A1 | 8/2004 | Weckwerth et al. | |
| 2004/0260209 A1 | 12/2004 | Ella et al. | |
| 2004/0260210 A1 | 12/2004 | Ella et al. | |
| 2005/0080465 A1 | 4/2005 | Zelickson et al. | |
| 2005/0177093 A1 | 8/2005 | Barry et al. | |
| 2005/0203592 A1 | 9/2005 | Teichert | |
| 2006/0047330 A1 | 3/2006 | Whatcott et al. | |
| 2006/0085223 A1 | 4/2006 | Anderson et al. | |
| 2006/0087864 A1 | 4/2006 | Peng et al. | |
| 2006/0095098 A1 | 5/2006 | Shanks et al. | |
| 2006/0140562 A1 | 6/2006 | Joseph et al. | |
| 2006/0173514 A1 | 8/2006 | Biel et al. | |
| 2006/0200211 A1 | 9/2006 | Lin | |
| 2006/0217787 A1 | 9/2006 | Olson et al. | |
| 2006/0235346 A1 | 10/2006 | Prescott | |
| 2006/0241495 A1 | 10/2006 | Kurtz | |
| 2006/0257095 A1 | 11/2006 | Walt et al. | |
| 2007/0021807 A1 | 1/2007 | Kurtz | |
| 2007/0079838 A1 | 4/2007 | Seckel | |
| 2007/0106192 A1 | 5/2007 | Johnson | |
| 2007/0129712 A1* | 6/2007 | Neuberger | A61B 18/24 606/15 |
| 2007/0129776 A1 | 6/2007 | Robins et al. | |
| 2007/0162092 A1 | 7/2007 | Yen | |
| 2007/0208395 A1 | 9/2007 | Leclerc et al. | |
| 2007/0208396 A1 | 9/2007 | Whatcott et al. | |
| 2007/0233208 A1 | 10/2007 | Kurtz et al. | |
| 2007/0233209 A1 | 10/2007 | Whitehurst | |
| 2007/0239232 A1 | 10/2007 | Kurtz et al. | |
| 2007/0255358 A1 | 11/2007 | Kahn et al. | |

(56) References Cited

U.S. PATENT DOCUMENTS

| | | |
|---|---|---|
| 2007/0260297 A1 | 11/2007 | Chariff |
| 2007/0282401 A1 | 12/2007 | Kahn et al. |
| 2008/0096857 A1 | 4/2008 | Curaudeau et al. |
| 2008/0103563 A1 | 5/2008 | Powell et al. |
| 2008/0119913 A1 | 5/2008 | Powell et al. |
| 2008/0125836 A1 | 5/2008 | Streeter et al. |
| 2008/0172112 A1 | 7/2008 | Gourgouliatos et al. |
| 2008/0198578 A1 | 8/2008 | Finn |
| 2008/0269849 A1 | 10/2008 | Lewis |
| 2009/0012586 A1 | 1/2009 | Kepecs |
| 2009/0024190 A1 | 1/2009 | Irvine |
| 2009/0054957 A1 | 2/2009 | Shanbaky |
| 2009/0076844 A1 | 3/2009 | Koegen |
| 2009/0088822 A1 | 4/2009 | Pruitt et al. |
| 2009/0099459 A1 | 4/2009 | Svanberg et al. |
| 2009/0099628 A1 | 4/2009 | Williams |
| 2009/0112296 A1 | 4/2009 | Weisbart et al. |
| 2009/0124958 A1 | 5/2009 | Li et al. |
| 2009/0132012 A1 | 5/2009 | Shanks |
| 2009/0185264 A1 | 7/2009 | Cameron et al. |
| 2009/0216219 A1* | 8/2009 | Venter .................. A61N 5/0616 606/11 |
| 2009/0216300 A1 | 8/2009 | Keltner et al. |
| 2009/0216301 A1 | 8/2009 | Streeter et al. |
| 2009/0254154 A1 | 10/2009 | De Taboada et al. |
| 2009/0319008 A1 | 12/2009 | Mayer |
| 2010/0056982 A1 | 3/2010 | Curaudeau et al. |
| 2010/0121419 A1 | 5/2010 | Douglas |
| 2010/0160904 A1 | 6/2010 | McMillan et al. |
| 2010/0241196 A1 | 9/2010 | Meyer |
| 2010/0242155 A1 | 9/2010 | Carullo, Jr. |
| 2010/0318161 A1 | 12/2010 | Brawn |
| 2010/0324632 A1 | 12/2010 | Lim et al. |
| 2011/0040355 A1 | 2/2011 | Francis |
| 2011/0066213 A1 | 3/2011 | Huttermann et al. |
| 2011/0087312 A1 | 4/2011 | Shanks et al. |
| 2011/0112613 A1 | 5/2011 | Gerlitz et al. |
| 2011/0143286 A1 | 6/2011 | Takada et al. |
| 2011/0144410 A1* | 6/2011 | Kennedy .............. A61B 18/203 600/2 |
| 2011/0176325 A1 | 7/2011 | Sherman et al. |
| 2011/0206752 A1 | 8/2011 | Carreno Serraima et al. |
| 2011/0212411 A1 | 9/2011 | Sinofsky |
| 2011/0218595 A1 | 9/2011 | McMillan |
| 2011/0245898 A1 | 10/2011 | Takada et al. |
| 2011/0270092 A1 | 11/2011 | Kang et al. |
| 2011/0301673 A1 | 12/2011 | Hoffer et al. |
| 2012/0116274 A1 | 5/2012 | Grasso, IV |
| 2012/0209359 A1 | 8/2012 | Chen et al. |

FOREIGN PATENT DOCUMENTS

| | | |
|---|---|---|
| CN | 2805814 Y | 8/2006 |
| CN | 1861215 A | 11/2006 |
| CN | 1879907 A | 12/2006 |
| DE | 38 30 517 C1 | 1/1990 |
| DE | 10 2010 023258 A1 | 4/2011 |
| EP | 0627243 A1 | 12/1994 |
| GB | 2532189 A | 5/2016 |
| WO | 2000/041768 A1 | 7/2000 |
| WO | 01/61240 A1 | 8/2001 |
| WO | 02095289 A1 | 11/2002 |
| WO | 2005/039338 A1 | 5/2005 |
| WO | 2006108093 A2 | 10/2006 |
| WO | 2010/026422 A1 | 3/2010 |
| WO | 2011/051467 A1 | 5/2011 |
| WO | 2011082420 A1 | 7/2011 |

OTHER PUBLICATIONS

LumiGram® Light for Style, © 2006-2008 LumiGram, http://www.lumigram.com/catalog/page5.php, accessed May 21, 2010, 2 pages.

Emirham, Kami, "Fiber Optics in Textile," 3rd International Symposium of Interactive Media Design, Jan. 5-7, 2005, 6 pages.

\* cited by examiner
† cited by third party

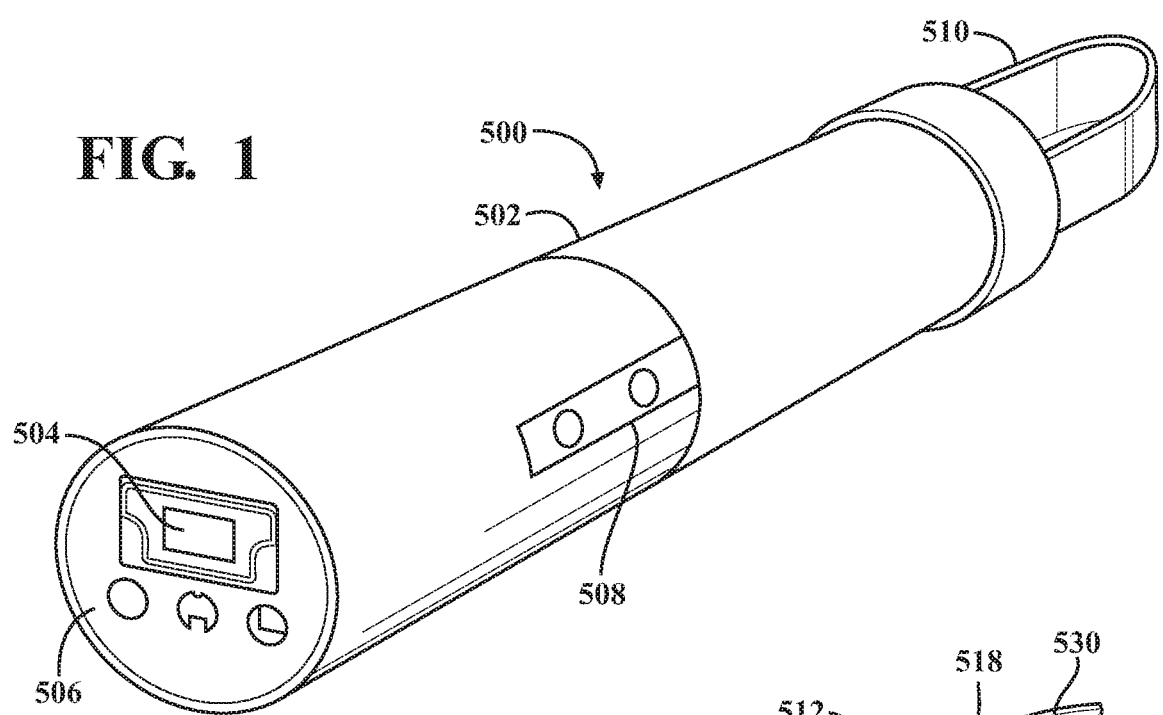
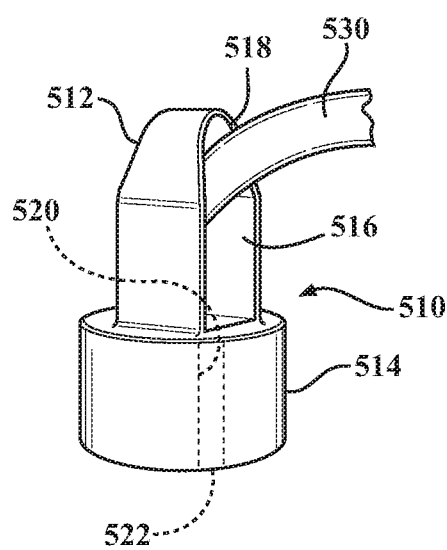
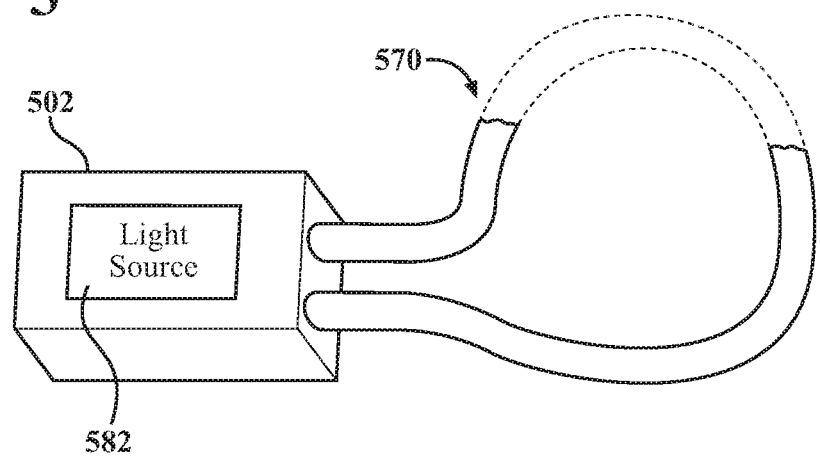

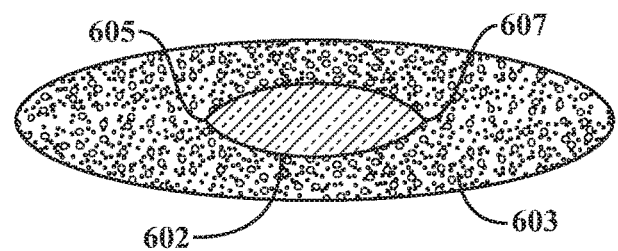
FIG. 14
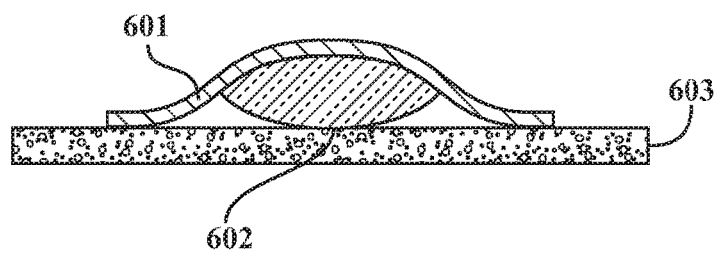
FIG. 14A
FIG. 15
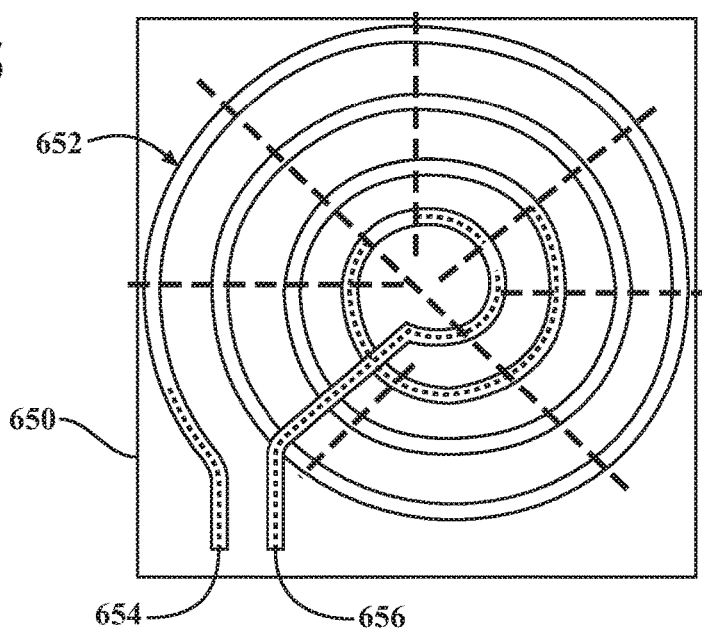

FIG. 19
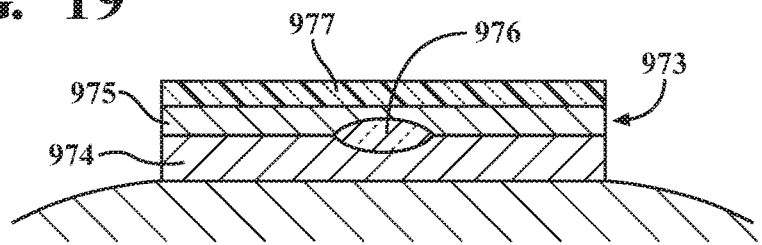
FIG. 20
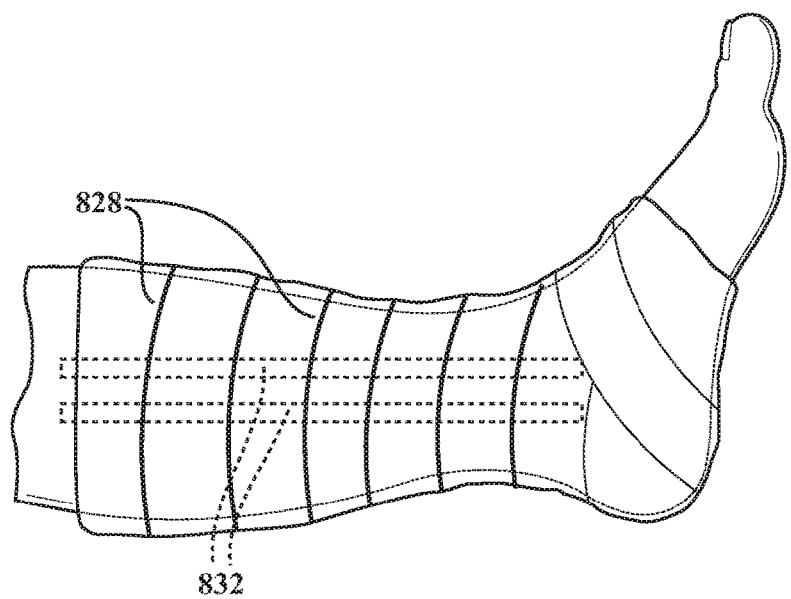
FIG. 21
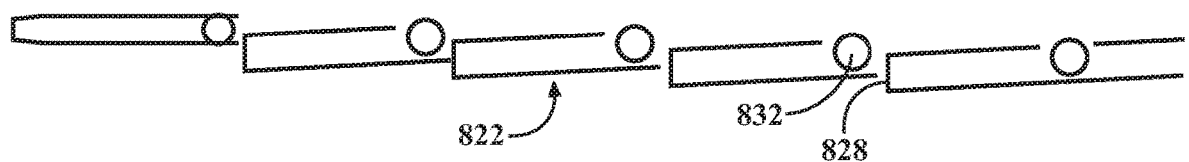
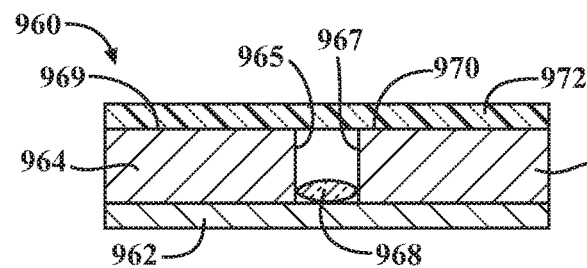
FIG. 22

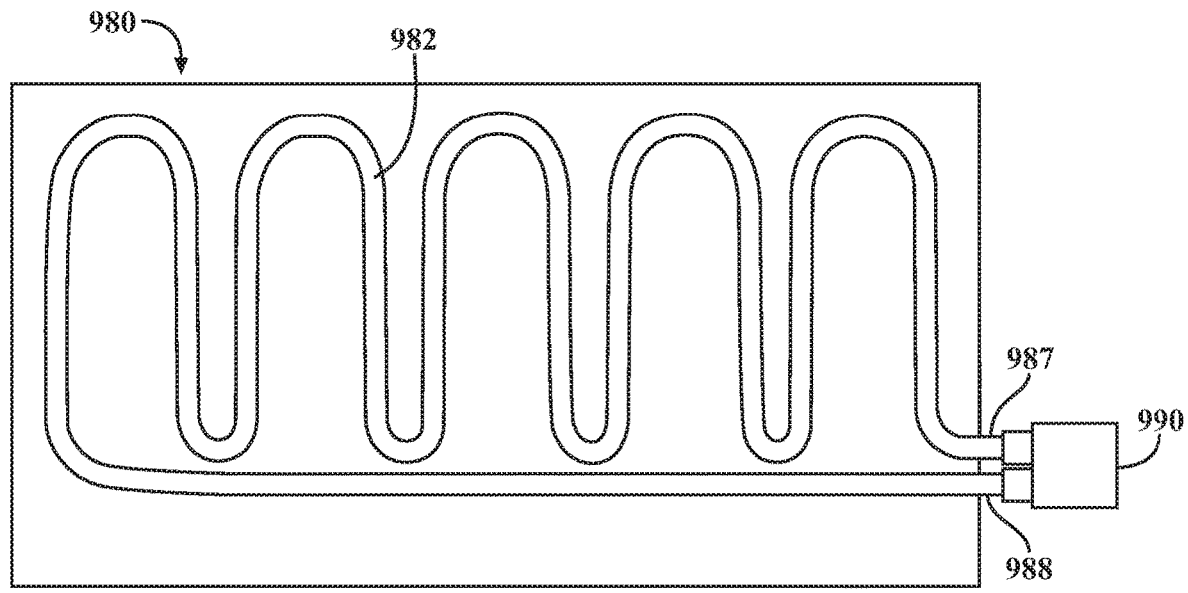
FIG. 23
FIG. 24
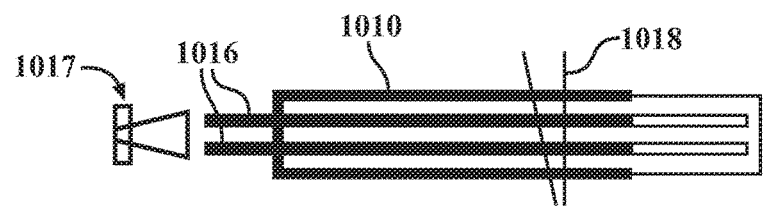
FIG. 25
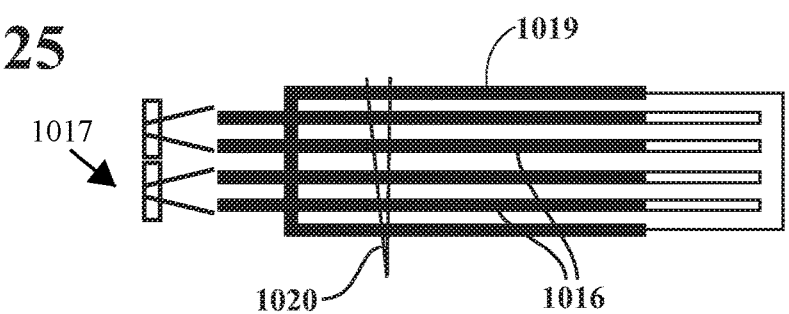

LIGHT THERAPY APPARATUS

CROSS-REFERENCE TO RELATED APPLICATION(S)

This application is a continuation of U.S. patent application Ser. No. 13/673,486, filed Nov. 9, 2012, which claims priority to U.S. Provisional Patent Application No. 61/557,604, filed Nov. 9, 2011, and No. 61/640,051, filed Apr. 30, 2012. The entire content of each of these applications is incorporated herein by reference.

BACKGROUND

Light therapy devices using light emitting diodes and laser diodes have been used for therapeutic application to humans for the treatment of various medical and physical disorders.

Fabric or textile products incorporating illuminated fiber optic fibers or rods interwoven by fabric threads and connectible to a light source have also been devised. Such illuminated fabrics have been incorporated into bandages for medical treatment as well as in articles of clothing for aesthetic purposes.

BRIEF SUMMARY

One implementation of a light therapy apparatus described herein comprises a housing, including an opening extending through a first surface of the housing from an interior of the housing, and a ramp extending from the opening at an upward angle to an opposed end at a higher elevation relative to a bottom of the housing than an elevation of a bottom edge of the opening, where the first surface perpendicular to the bottom of the housing. The light therapy apparatus also includes a laser mounted in the interior of the housing and facing the first surface of the housing at the higher elevation, and a control circuit that controls the laser according to a control program.

Variations in this and other implementations of the teachings herein are described in additional detail hereinbelow.

BRIEF DESCRIPTION OF THE DRAWING

The various features, advantages and other uses of this disclosure will become more apparent by referring to the following detailed description and drawing. Unless otherwise clear, like reference numbers refer to like elements.

FIG. 1 is a perspective view of one aspect of a light therapy apparatus.

FIG. 2 is a perspective view showing the coupling of a light guide to the retainer cap of the light apparatus shown in FIG. 1.

FIG. 3 is a pictorial representation of the attachment of a light guide to a housing containing a light source.

FIG. 14 is a cross sectional view showing a light guide mounted in a foam housing.

FIG. 14A is a cross sectional view of a modification to the structure of FIG. 14.

FIG. 15 is a perspective view of a spiral shaped light guide mounted on a pad.

FIG. 19 is a cross sectional view showing an alternate light guide and pad configuration.

FIG. 20 is a perspective view of another configuration of a light guide with a leg and ankle wrap.

FIG. 21 is a cross sectional view showing the individual wrap loops of the leg wrap shown in FIG. 18.

FIG. 22 is an end elevational view showing another aspect of the light guide and pad configuration.

FIG. 23 is a plan view of a light guide/bed pad application.

FIGS. 24 and 25 are plan views of alternate aspects of a light guide/pad configuration.

DETAILED DESCRIPTION

Figure 4:
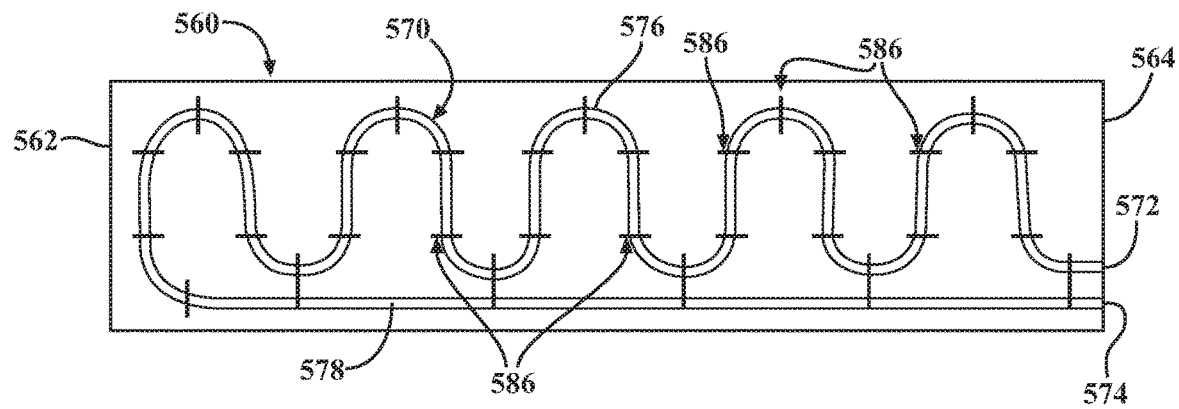
FIG. 4 is a top elevational view of one aspect of an elongated belt or pad carrying a light guide.

A laser light therapy apparatus is disclosed that uses a class II, III, or IV laser to produce class I laser output, thus enabling the apparatus to be used by ordinary people, without any training in the use of laser therapy apparatus. Class II, III or IV lasers often require skilled practitioner training and use.

Although the following description of the laser light therapy apparatus employs a class III laser power source, it will be understood that this is by example only as the laser light power source maybe any of a class II, class III or class IV laser light source. It will also be understood that the laser light source may be provided in any wavelength or color, as well as in visible, infrared, or ultraviolet wavelengths.

For example, one laser diode, such as a 150 mw-200 mw class III laser diode emitting 650 nm visible red light, can be employed. The laser means can also emit various light wave lengths including one of blue 405-435 nm for cosmetic applications, yellow/orange 590 nm for collagen stimulation, red 635-660 nm, and infrared 790-830. For specialized tools, a blue light at a wavelength 256 nm can be implemented to sterilize the light applicator coupled to the laser.

A control for the laser may be a circuit element which is operatively coupled to the laser diode and which controls the activation of the laser diode at a predetermined duty cycle or frequency over a predetermined time interval or number of time interval or intervals. For example, the control may be provided with circuit elements, or software instructions in the case of a central processing unit, which provide duty cycles of 50% and 75% selected by input buttons or touch screen points. The control also applies the duty cycle frequency of 50% or 75% to the laser diode for a predetermined time interval, such as 15 minutes, and is capable of repeating the time interval of application a selectable number of times over a given longer time interval, such as three times for every four hours, etc.

This periodic activation of the control provides significant advantages when employed with bandages, wraps, cast, etc. In such applications, the control, the laser means and optical media or light tubes are mounted in position on the patient to supply laser light energy to a selected portion of the user's body, such as a wound, the tissues surrounding a broken bone, and a broken bone itself; and separated from the patient's body, skin or wound by a thin porous gauze or fabric layer, as described hereafter.

The control executing its operational program can then activate the single laser or the dual laser at the appropriate duty cycle for a predetermined time interval, such as ten minutes. At the completion of the activation time interval, the control enters a sleep mode to reduce battery power drain. However, the control timer or clock continues to run to enable the control to awake and activate the laser(s) for a second time interval after a predetermined longer expiration of time, such as 4-6 hours.

This provides laser light therapy at predetermined intervals at a plurality of time spaced intervals throughout a 24 hour period, without user intervention. These multiple applications maximize the effectiveness of the laser light therapy. The control can also, in a dual laser assembly, where lasers having different wavelengths are employed, activate one laser for a first duty cycle, such as for a ten minute period and then the second laser at the same time or at a subsequent time interval, once for every predetermined 4-6 hour cycle. This may be advantageous in the case of a broken bone since the use of a red laser for one of the lasers will provide laser light energy to the tissue immediately below the skin; while the use of an infrared laser for the other laser, will provide laser light energy deeper within the patient's body to aid in healing the broken bone.

Referring now to FIGS. 1 and 2, there is depicted another example of a light therapy apparatus which is in the form a hand held holder or probe 500. The probe 500 is in the form of an elongated body or housing 502 having a front ferrule retainer cover or cap 510 for receiving the end of an optical light guide 530 and, at the same time, shielding the user's eyes from direct contact with the laser light output by the laser contained within the probe housing 502.

In this aspect, the modified front ferrule retainer cap 510 is provided for attachment to the laser output end of the probe 500. The cap 510 includes a cover 512 extending from a mounting collar 514. An internal sleeve 516 has an aperture 518 at one end. The aperture 518 opens to a through bore 520 extending through the sleeve 516 from the aperture 518 at one end to an aperture 522 at an opposite end within the mounting collar 514. The apertures 518 and 522 and the bore 520 provide a light path for laser light output from the probe 500 through the cover 510 while offsetting the external portion of the light guide 530 from the longitudinal axis of the laser light beam. In one example, the optical light guide 530 is in the form of a circular cross-section gel tube sold by Poly Optics Australia, PTY, Ltd. This optical member may be a generally gel-like polymeric, flexible tube or rod which has side scattering light characteristics. Such a tube may be formed of a continuous cross-section of the same polymeric material or may be provided with an inner core of a light reflective material surrounded an outer layer of the side scattering polymeric material. Light injected into one end of the polymeric tube from the probe 500 will be side scattered along the entire length of the tube to provide an illuminated display in the formed shape of the light guide 530.

The light guide 530 may or may not have a ferrule at one end for mounting within the end of the bore 520 in the cover 510 adjacent the second aperture 522. The light guide 530 is inserted through the first aperture 518 into and through the length of the bore 520 until it seats against a shoulder adjacent the second aperture 522. A tight friction fit may suffice to securely hold the fiber optic gel tube within the cover 510 in the proper dimensional relationship from the laser lens in the probe 500.

The rear portion or cap of the probe holder or housing 502 encloses interior circuit board which provides power from an onboard power source, such as batteries, or rechargeable batteries that can be recharged through a micro USB port 504 mounted on one end of the probe housing 502. The end 506 of the housing 502 may be removable to access the interior circuit board and batteries.

An on/off select switch 508 is mounted on the housing 502 to turn the laser on and off as well as to select modes of operation, such as continuous, flashing at different rates, etc.

One or two ends of a tube or light guide 530 can be coupled through the cap 510 to a single laser light source in the housing 502.

Figure 5:
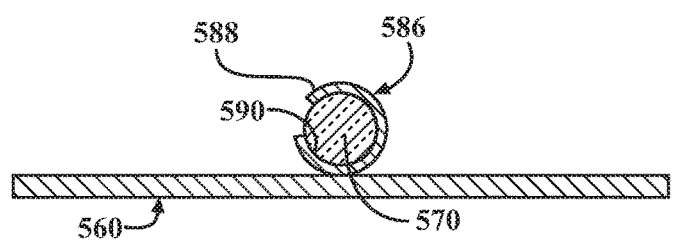
FIG. 5 is a side elevational view of the pad and light guide shown in FIG. 4.

Referring now to FIGS. 4 and 5, there is depicted another example of an illuminatable pad. In this aspect, by way of example only, the pad 560 is in the form of an elongated, strip like belt, which may function as a weight reduction or slenderizing, fat reduction belt. The belt 560 is formed of a suitable flexible material, such as nylon, leather, etc.

The belt 560 has opposed ends 562 and 564. Securing members, such as mating hook-and-loop fasteners, are formed on the inner and outer surfaces of the belt adjacent the first and second ends 562 and 564, respectively, to secure the belt 560 about the abdomen or waist of a user in a user desired degree of tightness as well as to adjust to different user waist diameters.

In this example, the light emitter can be an elongated polymeric tube 570 sold by Poly Optics Australia, Pty Ltd. However, the light tube 570 could also be a bundle of individual fiber optic rods or filaments.

The light tube 570 is mounted on the inner surface of the belt 560 in any desired arrangement. The illustrated arrangement of the light tube 570 having first and second ends 572 and 574, a sinusoidal or wave shape or segment 576 extending from the first end for a certain length before transitioning into a straight line segment 578 running to the second end 574 is shown by way of example only. However, the illustrated arrangement of the light tube 570 provides a substantially constant light intensity over the length of the light tube 570 suitable for light therapy application.

In the present example of the weight belt 560, a second light tube may also be mounted on the inside surface of the belt, in substantially the same sinusoidal and straight line segment arrangement as the first light tube 570. The ends 572 and 574 of the light tubes 570 may be ferruled or, in the case of the gel tube, merely inserted into a suitable holder or mount in light source housing 502, as shown in FIG. 3. The ends 572 and 574 of the light tube 570 are spaced in the desired light transmission dimensional relationship with a light source lens. The tight side-by-side grouping of the ends 572 and 574 of the light tube 570 are approximately equal in cross section to the cross sectional area of the lens. This enables from the light source 582 in the housing 502 to be projected into both ends 572 and 574 of the light tube simultaneously. In this manner, equal amounts of light are transmitted along opposite segments of the light tube 570 thereby providing a sufficient length of a predetermined amount of light intensity along the length of both segments of the light tube 570. This overcomes the inherent resistance in the light tube 570, when formed of a gel tube or fiber optic rods, which causes decreasing amounts of light to be output for increasing length of the tube or rods.

The light tube 570 can be removably mounted on the inner surface of the pad or belt 560 by many different mounting means, including tape, stitching, or, as shown by way of example only in FIGS. 4 and 5, a series fasteners or clips 586 secured by adhesive, stitching, ultrasonic welding, etc., to the inside surface of the belt 560 in a desired dimensional relationship and arrangement.

As shown in detail in FIG. 5, each fastener 586 is in the form of a small clip having spaced, separable ends 588 and 590 that spread apart as the light tube 570 is forced between the ends 588 and 590 and then snap back into their nominal position to tightly, but removably secure the light tube 570 in the clip 586.

In the illustrated arrangement of the clips 586 in FIG. 4, the light tube 570 can be gradually looped back and forth through the clips 586 to form the sinusoidal or wave segment 576 and then the generally straight line segment 578.

The ends 572 and 574 of two light tubes 570 for a longer length belt can be coupled to a suitable light source in a holder which also carries or is coupled to a power source, such as a replaceable and/or rechargeable battery. The light source holder and battery compartment may be mounted on the inside surface of the belt 560 or the ends 572 and 574 of each light tube 570 may be passed through apertures in the belt 560 and coupled to a light source holder and battery pack mounted on the outside surface of the belt 560.

In the illustrated example, the location on the belt 560 between the two light tubes 570 can be placed at the front center of a user's abdomen. The end of the belt 560 carrying the first light tube 570 is extended around the left side of the user's abdomen. The portion of the belt carrying the second light tube 570 is then wrapped around the right side of the user's abdomen. The free end 564 of the belt 560 is wrapped around the user's waist, the first end portion of the belt 560 and around the intermediate portion of the belt 560, depending upon the diameter of the user's waist, until the desired tightness of the belt 560 around the user's waist or abdomen is achieved. The end portion of the belt 560 extending from the second end 564, which can carry a hook-and-loop fastener, is then secured to a hook-and-loop fastener on the outer portion of the belt 560 to tightly secure the belt 560 in position around the user's abdomen or waist.

In this position, the two light tubes 570 are positioned to provide light therapy to the front portion and the side portions of the user's abdomen, again depending upon the size of the user's waist. The belt 560 may be shifted around the user's waist to provide light therapy to other portions of the user's waist, such as the user's back, if desired.

Figure 6:
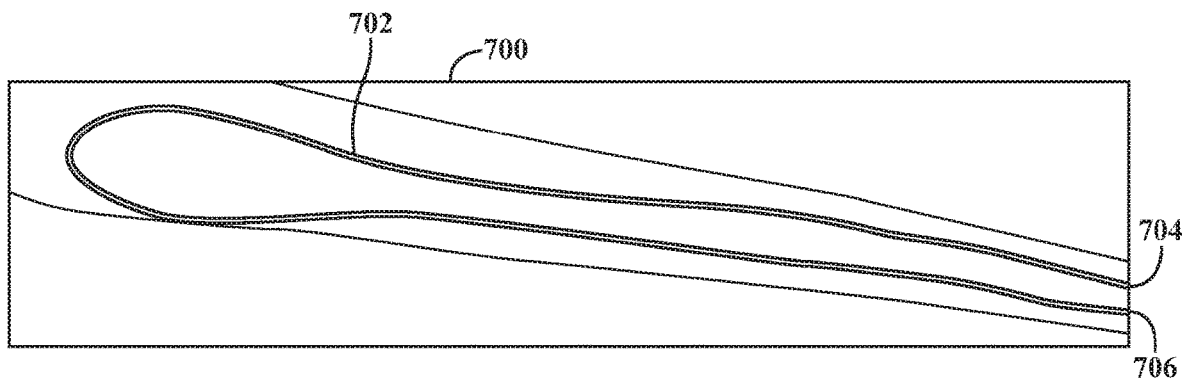
FIG. 6 is a top elevational view showing another application of a light guide on an elongated pad.

FIG. 6 depicts an alternate laser apparatus arrangement on an elongated strip or belt 700. In this arrangement, the polymeric light guide or tube 702 is mounted in a simple elongated loop with both open ends 704 and 706 located in proximity with each other, typically adjacent one end of the belt 700.

Figure 7:
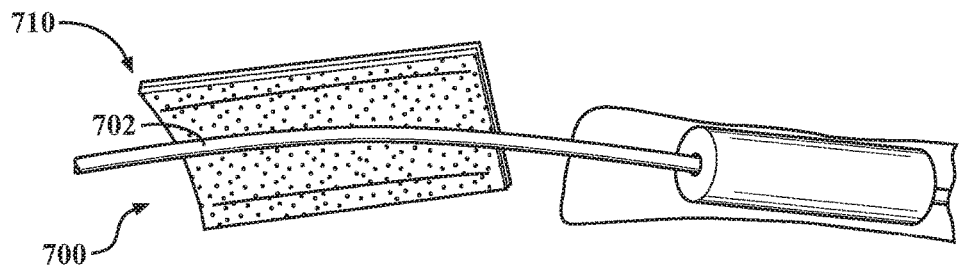
FIG. 7 is pictorial representation of another aspect of a light guide mounted on a pad and coupled to a power and control housing.

Narrow loops can be wrapped around the light tube 702 at various spaced locations to provide mounts for securing the tube 702 to the strip or belt 700. The loops provide a convenient mount for stitching to securely attach the light tube 702 to the belt 700 in the illustrated configuration. Alternately, as shown in FIG. 7, a unique mounting strip 710 is employed to secure the light tube 702 at spaced locations on an inner surface of the belt 700.

The mounting strip 710 is formed of two layers, including a first layer which is configured to be placed adjacent to the inner surface of the belt 700 and a spaced outer layer which is configured for facing the patient's body when the light tube 702 and the mounting strip 710 are mounted on the inner surface of the belt 700 and the belt 700 wrapped around the desired location of the patient's body. The first and second layers may be formed of separate layers in the same or different materials which are joined at one common edge by adhesive, heat welding, stitching, etc. Alternately, the first and second layers may be formed of the same material with the second layer merely forming a portion of the first layer which is wrapped around the light tube guide 702.

Both of the first and second layers of the mounting strip 710 may be formed of a suitable medical grade material, such as a medical grade vinyl. One or both of the material layers may be formed of a transparent medical grade vinyl or, in one aspect, the second or outer layer of the flash strip may be formed of a transparent vinyl and the inner or first layer formed of a light reflective material, such as a white or otherwise reflective vinyl.

In either configuration, the outer ends of the layers are overlaid on each other and then secured together by an attachment means, such as thread stitches, heat welding, adhesive, etc.

The mounting strip 710, since it surrounds the light guide 702, may be slid longitudinally along the length of the light guide 702 to any desired location for attachment to the belt 700.

The completed mounting strip 710 may be mounted to the inner surface of the belt 700 at spaced locations by thread stitching, adhesive, etc. Alternately, the means for joining the ends of the material layer together can also be used to attach a hook-and-loop fastener to one side of the first layer. The hook-and-loop fastener can removably adhere to the inner surface of the belt, if the inner surface of the belt has a fuzzy surface. Alternately, mating hook-and-loop fasteners may be mounted at various locations along the length and width of the belt 700. Alternately, a slot can be formed in a tight fitting garment, such as a shirt, pants, etc., to apply light therapy to the body meridians or for orthopedic applications.

Figure 9:
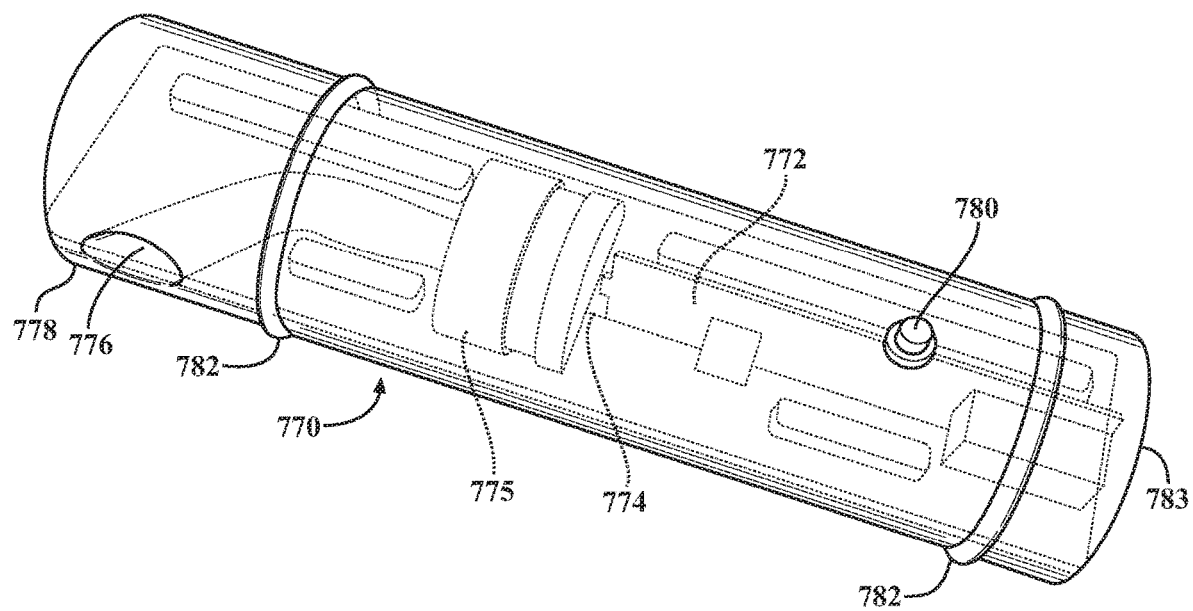
FIG. 9 is a partially broken away, perspective view of another aspect of a light therapy apparatus housing.

It should be noted that in the light therapy apparatus shown in FIG. 9, the laser does not have a lens, commonly used with all light therapy lasers. Rather, the laser uses the light tube as a focusing means. The lack of a lens on the laser reduces coupling losses thereby enabling a lower powered laser, then would typically be required, to output sufficient light for a longer length of the light tube.

In this aspect, the housing 770 includes two mating halves which are provided with internal recesses for mounting a printed circuit board 772, a single laser light source 774, and a heat sink 775, and a curved bore 776 communicating between the light source 774 and an open end 778. A control switch or push button 780 is mounted on one edge of the printed circuit board 772 and extends through an aperture formed in one of the halves of the housing 770 for activating or turning off the control circuitry on the printed circuit board 772.

Retainers, such as elastic O-rings 782, are removably mounted in external grooves on the two halves of the housing 770 to retain the two halves of the housing 770 together.

The housing 770 provides a convenient hand held configuration for easy use of the laser therapy apparatus. A power connector 783 can be mounted at one end of the housing 770 and connected to the printed circuit board 772. The connector 783, which can be a USB-type connector, can be coupled via a suitable electrical conductor or cord to a remote power source, such as a computer, MP3 player, battery, etc.

Alternately, the housing 770 maybe coupled to longitudinally arranged power supply housing, not shown, to form an elongated hand held apparatus. The power source housing can contain one or more batteries which are coupled through suitable contacts and connectors in the power supply housing to the printed circuit board 772.

The above described aspects of the present light therapy apparatus can be employed in a number of different applications. For convenience, these applications are referred to as small, medium, and large applications with variables being the laser wattage, the gauge or diameter of the light tube, and the light tube length.

Small applications of the light therapy apparatus can be used for wrist and elbow pads or formed bans, similar to that shown in FIGS. 10-15. These applications require only a short length light tube of approximately six to twelve inches and thereby are suited for the small size housing 770 or 500 with onboard or remotely connected power sources.

Medium size light therapy apparatus are suitable for joint/back, lower abdomen, facial cosmetics, and hair therapy applications as well as broken bone therapy. These applications require a longer length light tube and increased laser power as well as a larger diameter light tube. Such medium size applications may typically require two laser light sources coupled to both ends of a single continuous light tube.

Larger size light therapy apparatus can include the belt 700 as well as bed pads described hereafter. These large size applications require the largest laser power requirements and light tube lengths. It should be noted that individual laser housings 770 or 500 may be serially coupled together to provide power for such large applications, particularly bed pad applications.

In addition to the mounting of a light tube 570 in a strip 560 in the form of a weight belt, a similar light tube, power source, light source and mounting configuration may be applied to other shaped pads so as to apply light therapy to different parts of the user's body. For example, the strip or pad 560 could be in the form of a smaller length strip which is mountable over a person's elbow, wrist, knee or ankle. The light tube is mounted, in one or more loops or other arrangements, on or in the pad to provide the desired light therapy to the particular region of a user's body.

Figure 10:
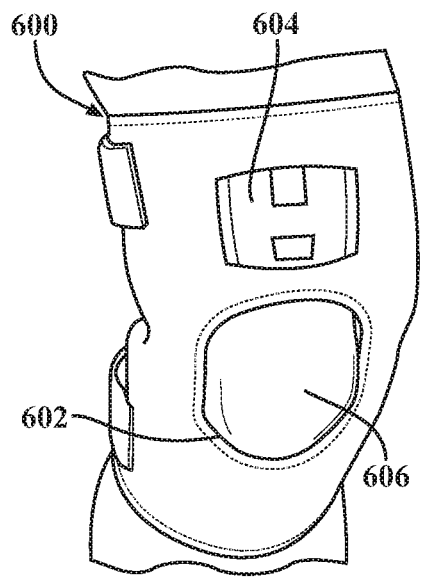
FIGS. 10 and 11 are perspective views of different aspects of a light guide applied to a knee support.

For example, a knee pad 600 is shown in FIG. 10. The knee pad 600 has a light tube 602 formed in a circular loop and mounted around a front positioned knee hole 606. The light source and power supply 604 may be mounted in a small housing on the front of the knee pad 600 at any suitable location, such as at a location for easy connection to the ends of the light tube 602.

Figure 11:
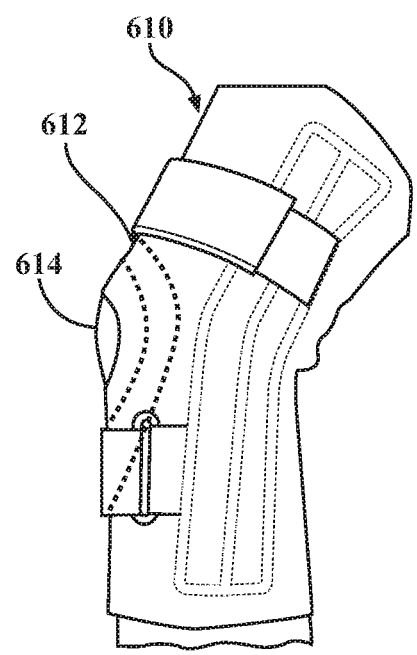

A similar knee pad 610 is shown in FIG. 11. In this aspect, the light tube 612 is formed in two circular loops about the front positioned knee hole 614.

Figure 12:
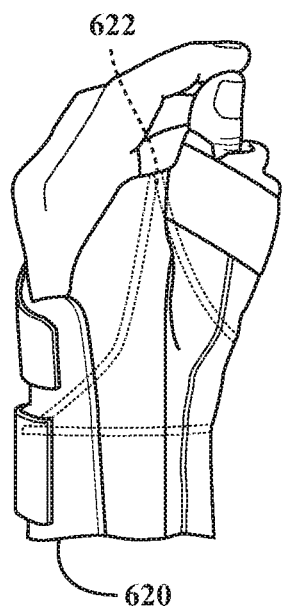
FIG. 12 is a perspective view showing the application of a light guide to a wrist support.

A wrist support 620 is shown in FIG. 12. A light tube 622 is suitably attached or fixed within or on the wrist support 620 and disposed in a looping arrangement around the user's thumb and wrist.

Figure 13:
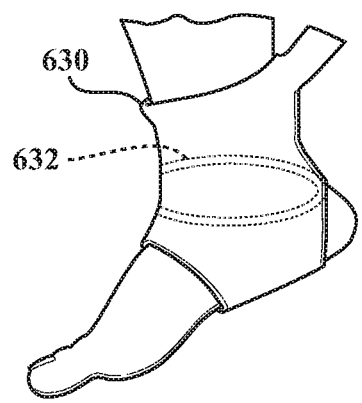
FIG. 13 is a perspective view of one aspect of the application of the light guide to an ankle wrap.

An example of an ankle support 630 is shown in FIG. 13. A light tube 632 is mounted on or carried within the ankle support 630 and disposed in a single, generally oval shaped loop wrapping around the front upper most portion of the user's foot and ankle. Alternately, the light tube 632 could be formed in a continuous circular loop about the entire periphery of the user's ankle.

In all of the pads or supports 600, 610, 620 and 630, shown in FIGS. 10-15, the ends of the various light tubes are attached to a light source housing and power supply which is suitably attached to or mounted in the supports at a convenient location for stability during user mobility as well as to provide easy access to the on/off switch and other controls on the light source housing, as described above.

Figure 8:
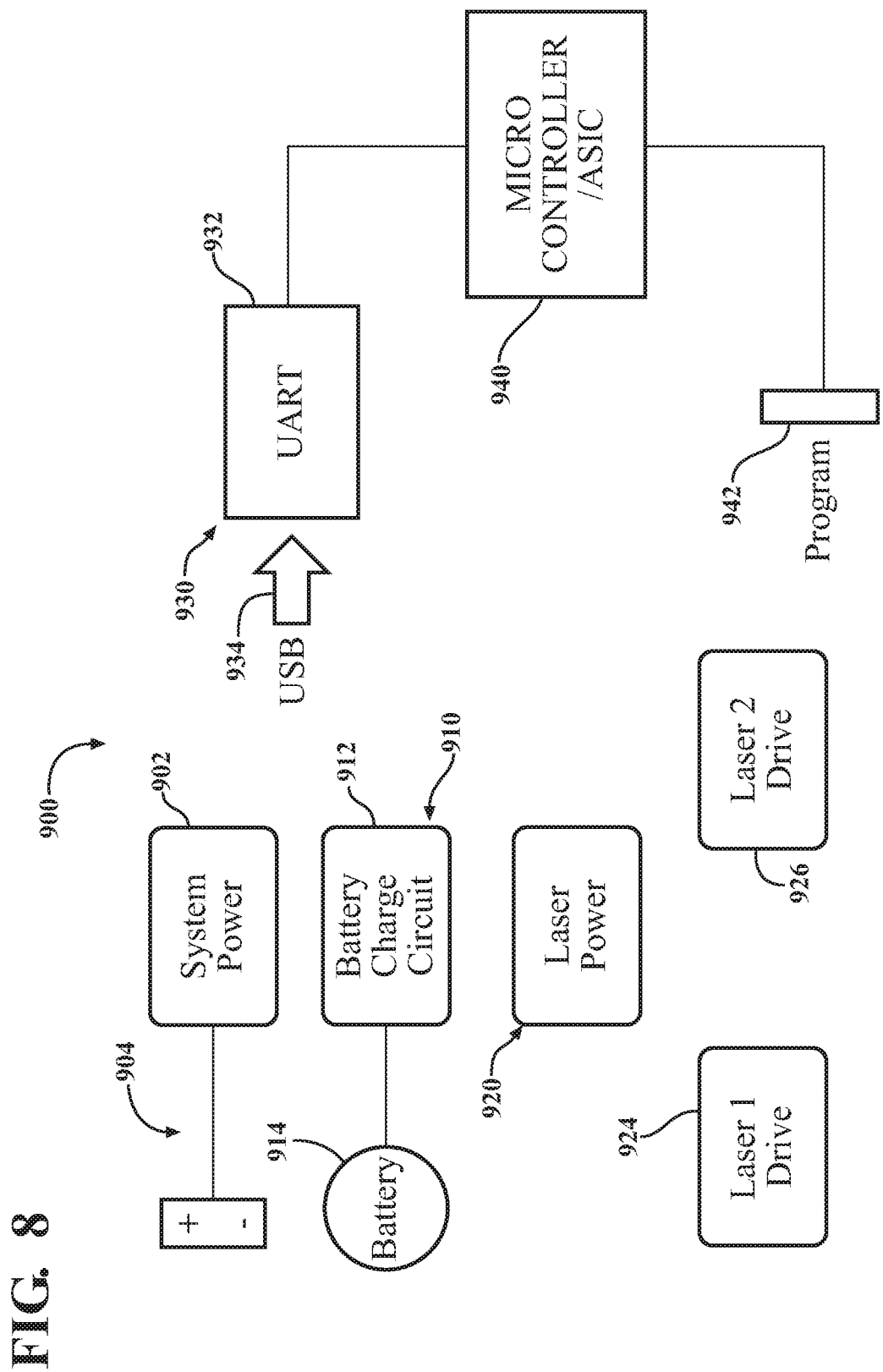
FIG. 8 is a schematic block diagram of the power and control circuitry employed in the housing of FIG. 9.

In any use of the light tube, such as the light tubes 602, 612, 622 and 632 in the body support shown in FIGS. 10-15, as well as on the belt shown in FIGS. 5 and 8, the light tube, such as light tube 602 as shown in FIG. 14, can be mounted within and completely encompassed by a sheath or a layer 603 of a soft, resilient foam material. The foam can be any type of closed cell or open foam, such as hydrophilic cell foam, which exhibits some degree of rigidity, while still being slightly compressible. The elongated, generally oval-shaped cross-section for the foam layer 603 shown in FIG. 14 provides an enlarged surface area around the light tube 602 thereby preventing the small diameter light tube 602 from creating an uncomfortable bump when in contact with the user's skin.

The side edges 605 and 607 of the light tube 602 taper to a point to minimize discomfort or bed sores for a user lying on the pad.

At the same time, the foam layer 603 exhibits light transmission properties to enable the light generated through the light tube 602 to pass outwardly from the foam layer 603 on the user's skin. The foam layer 603 also diffuses the light from the light tube 602 over a larger area.

It is also possible to add a reflective layer 601 on one side of the light tube 602, as in FIG. 14A, or along one edge of the foam layer 603 to reflect light generated in one direction by the light tube 602 back through the foam layer 603 onto the user's skin. Silky adhesive mechanical tape provides excellent reflective properties. The reflective layer would typically be applied on the surface of the foam layer 603 and which is disposed outwardly; not in contact with the user's skin. The foam layer 603 can be formed about a centrally located light tube 602 in a mold, for example. The foam layer 603 can also be formed by other methods, such as by preforming the foam layer, slicing it into two longitudinal sections and hollowing out a central portion for the light tube 602. The split edges of the foam layer 603 surrounding the light tube 602 can then be adhesively rejoined to form a sealed, moisture proof enclosure about the light tube 602.

The foam layer 603 should be thick enough or have a particular degree of compressibility so that when the foam layer 603 is in a compressed state in its mounting position on a body support or belt and in contact with or adjacent to the user's skin, the thickness of the compressed foam layer 603 is greater than the diameter of the light tube 602.

FIG. 15 depicts a generally flat flexible pad 650. A light tube 652 with opposed ends 654 and 656 is attached to the pad 650 and arranged in any suitable configuration to provide substantially even light over a substantial portion of one surface of the pads 650. As illustrated in FIG. 15, the light tube 652 is arranged in an inward extending circular spiral extending from the first end 654 to the second end 656. Such a pattern can be achieved by embroidering the tube onto a piece of polyester translucent cloth and/or affixing the light tubing to a porous adhesive coated substrate. A piece of foam is then placed over the substrate, adhering to it, or if the cloth is used, it may be encased in foam on both sides and then sealed on the edges by sewing, ultrasonic seam or medical grade adhesive.

The ends 654 and 656 of the light tube 652 are connected to a suitable power and laser light source pack or housing, as described above. The housing, not shown in FIG. 15, may be mounted at any convenient location on or immediately adjacent to the pad 650 in relation to the ends 654 and 656 of the light tube 652. The position of the housing is selected for durability as well as easy access to the housing controls.

The pad 650 and the light tube 652 is ideally suited for use in providing light therapy to large regions of a user's body, such as the user's back or lower abdomen. Alternately, the pads 650 can function as a bed pad, with the user laying on his or her stomach or back for light therapy application.

Larger and/or different shaped pads, as well as different means for securing the pads on a user's body may also be employed to provide light therapy using the illustrated light tubes for an individual's shoulder, chest or back.

The pad 650 shown in FIG. 15 may also be made in a small overall size and mounted on the inside surface of a cap or hat, such as a baseball cap. The generally circular, spiral arrangement of the optic media or light tube 652 enables the light tube 652 to conform to the spherical shape of the user's head and provide a substantially even distribution of light intensity over the entire covered portion of the user's head or scalp. This may be particularly advantageous in light therapy applications for baldness.

Any of the pads 600, 610, 620, 630 and 650, may be formed by embroidery in which threads are embroidered over, under and around the light tubes to form the pad in the desired overall shape. In this pad construction, the light tube or optic media forms an integral, secure part of the pad.

Particularly in constructions where the optic media is formed of the gel tube, the entire pad, after the light source housing and power supply have been disconnected from the ends of the optic tube, can be washed without damage to the light tube.

An example of a circuit 900 which can be used to control and supply power to one or more lasers is illustrated in FIG. 8. The circuit 900 includes a system power supply circuit 902. The circuit 902 includes an on/off switch 904, which turns the entire laser and power control device on and off.

A battery recharge circuit 910 includes a regulator circuit 912 which supplies regulated power to recharge a storage battery 914 in the housing.

One or two laser power circuits 920, in the case of a light therapy apparatus having two lasers, power individual laser drive circuits 924 and 926, respectively.

The control circuit also includes a signal circuit 930 utilizing a universal asynchronous receiver/transmitter circuit (UART) for translating data sent to or from the circuit 900 between parallel and serial forms through, e.g., a USB connector 934. The UART 932 is coupled to a control circuit 940 which can be a micro controller or an ASIC which operates a control program 942 which can be stored in memory or otherwise programmed into the ASIC for controlling the operation of the circuit 900.

Figure 16:
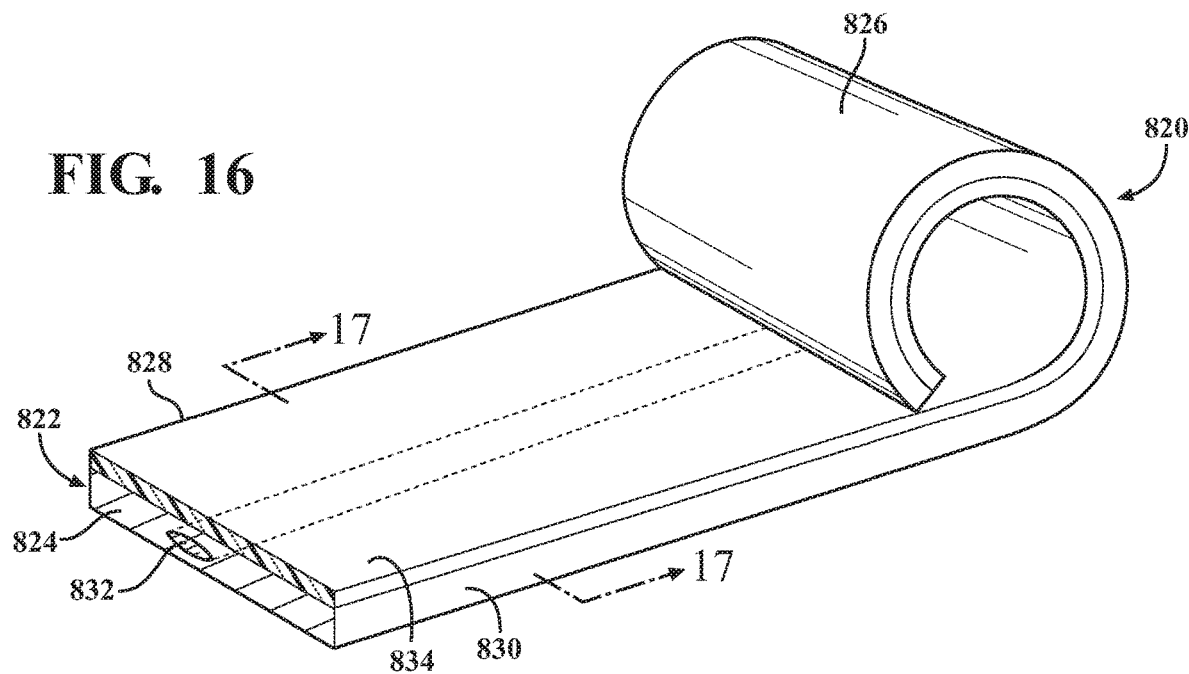
FIG. 16 is a perspective view showing yet another aspect of a laser light guide and foam pad configuration.
Figure 17:
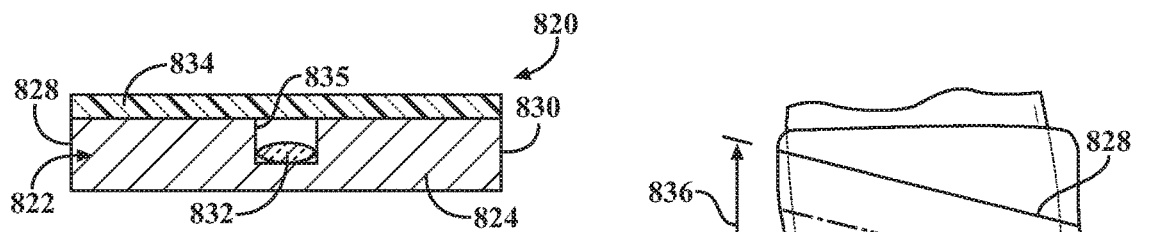
FIG. 17 is a cross sectional view generally taken along line 17-17 in FIG. 16.
Figure 18:
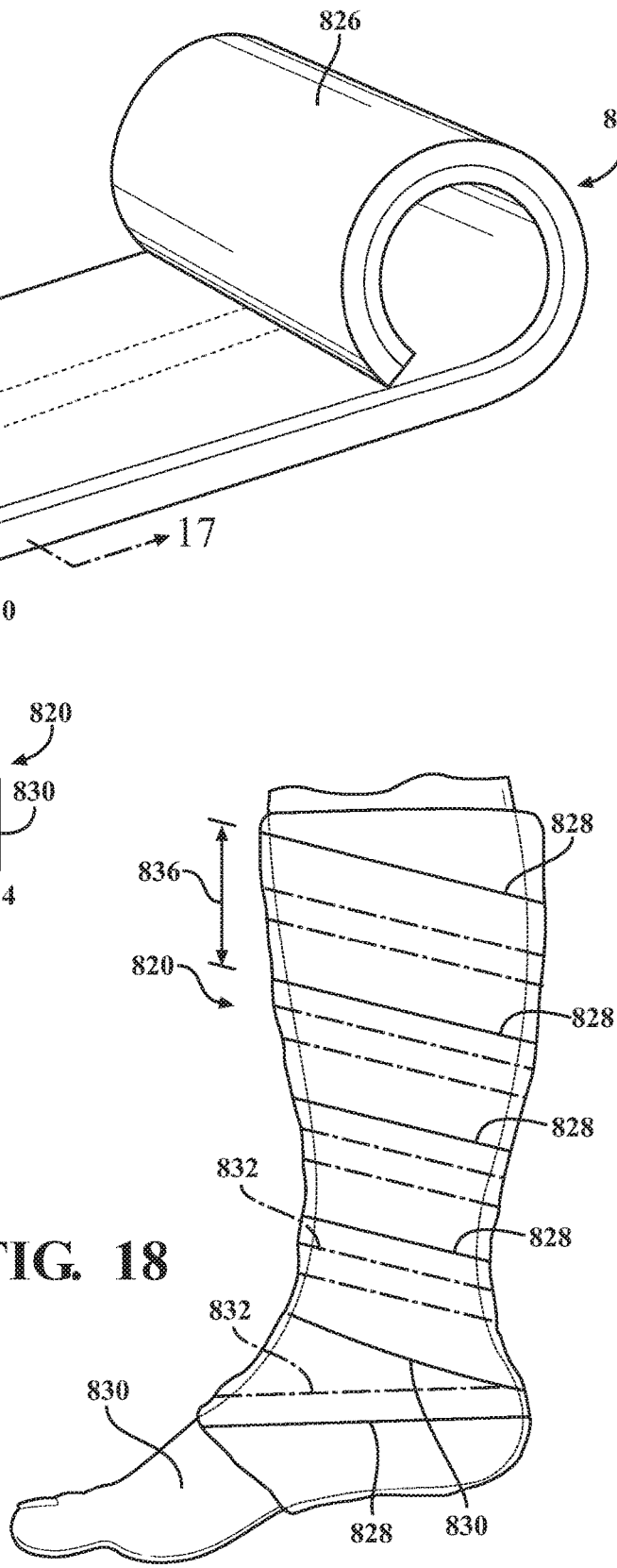
FIG. 18 is a side elevational view showing the application of a light guide in a leg wrap.
Figure 26:
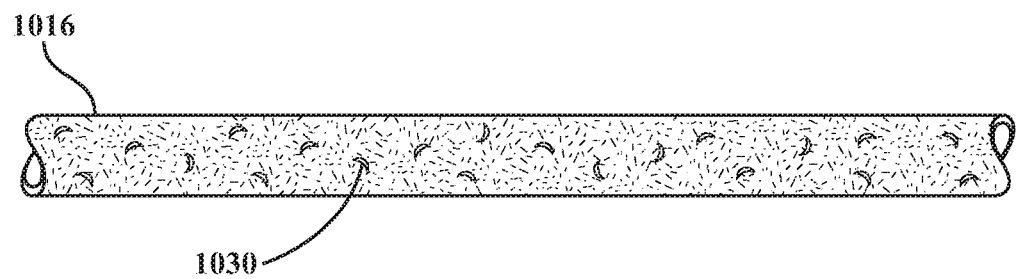
FIG. 26 is a side elevational view of another aspect of a light guide.

Referring now to FIGS. 16-18, there is depicted another aspect of a laser light therapy apparatus in the form of an elongated, flexible strip which can be wrapped in multiple turns around a portion of a user's body, such as user's limb, with the user's lower leg and ankle shown in FIG. 26 by way of example only.

In this aspect, the light therapy apparatus 820 includes a flexible medical grade material strip, such as a cotton batten strip 822 in the form of an elongated strip having a first end 824, an opposed second end disposed within a roll 826 and opposed side edges 828 and 830. A light tube 832, such as any of the light guides described above is provided for the apparatus 820.

A thin sheer layer 834, which may be formed of mostly clear-type polyester, acts as cover over the light tube 832. The sheer material layer 834 can be laminated, bonded, sewn or adhered to another substrate, such as the cotton batten layer or strip 822.

The sheer layer 834 has a high porosity to allow for breathability to enable the patient's skin to breath or, if used under a negative pressure wound bandage, allows a vacuum to suck the exudate from a wound through the sheer layer 834. According, the sheer layer 834 may also be referred to as a porous layer 834.

The thickness of the layer 822 is greater in a compressed state than the diameter of the light tube 832. This recesses the outer most edge of the light tube 832 below the outer surface of the layer 822 to prevent a bump from being formed in the sheer layer 834 when the sheer layer 834 is fixed to the layer 822. A recess 835 is thus formed in the layer 822 when the light tube 832 is rolled or otherwise forced into the layer 822. The recess 835 may also be pre-formed by rolling or molding into the layer 822, depending upon the material used to form the layer 822.

An alternate strip construction is shown in FIG. 22. In this aspect, a strip 960 is formed of a thin base layer 962 of a soft, flexible material, such as cotton. Two sponge foam or cotton cloth strips 964 and 966 are mounted with spaced inner edges 965 and 967, respectively, to the base layer 962 by adhesive, for example. The adhesive may be separately applied to the strips 964 and 966 or the base layer 962 or provided in a self-stick layer pre-applied to the base layer 962 on one surface of the strips 964 and 966. Alternately, a single foam or cotton strip and light-colored medical tape to adhere the light tube to the strips can be used.

The inner surfaces or edges 965 and 967 of the strips 964 and 966 respectively, are spaced apart a distance substantially equal to the diameter of a light tube 968. However, the height of each strip 964 and 966 is greater than the diameter of the light tube 968 when the strips 964 and 966 are in a compressed state so as to maintain an outer edge of the light tube 968 below an upper surface 969 and 970, respectively, of each strip 964 and 966. This prevents contact between the light tube 968 and a patient's body when the strip 960 is mounted in a tightly wrapped or compressed state about the user's body.

Finally, a thin outer layer 972 of a porous cloth material, which is medically wound friendly, is secured over the upper surfaces 969 and 970 of the strips 964 and 966. The suitable adhesive, thread stitching, heat welding, etc., may be used to secure the layer 972 to the strips 964 and 966.

Depending upon the application, the width of the strips 822 and 960, with only one strip 822 described here, between the lateral side edges 828 and 830, may be provided in different dimensions, such as two inch width, a three inch width or a four inch width. The medical benefit of the narrower two inch wide strip is that it delivers twice as much light over the point of interest than the wider four inch strip. The overall length of the strip 822 may also be variable, with a 72 inch strip length being an example.

With the light tube 832 disposed in a control position between the lateral side edges 828 and 830, the entire apparatus 820 may be wound in a plurality of turns around the user's limb, such as the user's calf, shown in FIGS. 18 and 21, to provide a predetermined spacing between adjacent turns of the light tube 832. The spacing 836 of adjacent turns of the light tube 832 along the length of the user's limb depends on the width of the apparatus 820. For a four inch wide apparatus 820 (i.e., distance between the lateral side edges 828, 830), for example, the spacing 836 between adjacent turns of the light therapy apparatus 820 may be two inches. For a three inch wide apparatus 820, a one-half inch spacing may be provided between adjacent turns of the light tube 832. For a two inch wide apparatus 820, one inch spacing between adjacent turns of the light guide 832 may be used.

In an alternate construction, also shown in FIG. 22, the bottom or base layer 962 as well as the top or outer layer 972 can be formed of non-woven polyester cloth. The inner strips 964 and 966 can be formed of a medical grade hydrophilic polyurethane foam. Such a foam is absorbent and porous for ideal use to absorb from wounds.

In yet another aspect, the top outer layer 972 can be formed of the medical grade hydrophilic polyurethane foam. The bottom or base layer 962 can be formed of non-woven polyethylene cloth. The intermediate disposed strips 964 and 966 and again formed of polyurethane foam.

In yet another aspect, the entire pad 820 can be formed of medical grade hydrophilic polyurethane foam, including the bottom base layer 962, the intermediate strips or layers 964 and 966 from the top layer 972.

In yet another aspect, medical grade hydrophilic polyurethane foam can be used to form the top to bottom layers 972 and 962. Medical grade hydrophilic polyurethane foam which incorporates a layer of a polyethylene mesh can be used for the intermediate strips or layers 962 and 964.

Using foam for one or more layers of the bandage or support offers a light dispersion therapeutic benefit in addition to a dispersion of a potential pressure point caused by the light guide tube, which would be adverse to pressure wound healing. For example, an optical bandage or support using a 3 mm diameter light tube with an exterior layer of cloth would have a wound dispersion area 3 mm wide. Yet, the same 3 mm diameter light tube is encased in 3 mm thickness of foam; the light is dispersed minimally over twice the surface area or effectively 6-8 mm.

For knee, ankle, elbow or wrist braces described above, the use of ¾-1 inch foam tubes, having a round or oval cross section, provide an improved light dispersion area of up to five times that of a simple uncased light tube, while simultaneously providing the increased user comfort.

Referring back to FIG. 18, starting from the end of the light tube 832, which is disposed immediately adjacent to the laser in the power and light source housing, the initial portion of the light tube 832 will have the greatest light intensity with further portions of the light tube 832 being of slightly less intensity. The initial portion of the light tube 832 desirably overlays the large artery in the ankle, which exposes the user's blood flowing through the large artery to the greatest light intensity for maximum therapeutic effect on the user's blood.

The strip 822 or 960 may also be used as an inner layer of a compressive wound wrap. When used as the inner layer of a multi-layer compressive wrap, the light tube 832 or 968 is disposed immediately adjacent to the user's skin or wound, but is separated from the wound or skin by the porous layer 834 or 972 of the strips 822 and 960 to allow light from the light tube 832 or 968 to pass through to the patient's wound or skin; while allowing exudate from the user's skin to pass through the porous layer 834 or 972.

Alternately, as shown in FIG. 20, the optical light guide or tube 832, which can be provided in one, two or more elongated strips, may be disposed generally perpendicular to the edges 828 of the exterior wrap and generally parallel to the longitudinal axis extending through the user's limb. This arrangement provides light therapy to a substantial length of the veins and arteries for enhanced therapeutic benefits.

An alternate optical bandage or pad construction is shown in FIG. 19. In this aspect, an inner layer of a porous foam material, as described above, is provided for contact with a user's limb or skin. An adjacent layer of foam 975 is provided in a stacked arrangement with the first foam layer 974. The soft resilient nature of the foam layers 974 and 975 enable a light guide or tube 976 to be sandwiched between adjoining faces of the two foam layers 974 and 975 and compress the foam layers 974 and 975 to minimize a noticeable increase in height of the stacked foam layers 974, 975. An outer layer 977 of an adhesive material can be applied over the topmost foam layer 975. The adhesive layer 977 increases the light reflectivity from the light guide 976 to the user's limb as well as allowing the pad to adhere to itself as it is wrapped about the user's limb.

It should also be noted, in FIG. 19, that the light guide 976, rather than having the previously illustrated generally circular cross section, is in the form of a shallow oval or a rectangle with smoothly curved corners. This aids in reducing any noticeable increase in the height of the pad 973 shown in FIG. 19 to minimize uncomfortable contact with the user's limb and to prevent bed sores if the user is lying on the pad 973.

The light therapy apparatus may also be formed as a bed pad as shown in FIG. 23. Any of the multi-layer pad or strip arrangements described above may be employed for a bed pad 980. The bed pad 980 has a square or rectangular configuration, such as a rectangular configuration of twelve inches wide by eighteen inches long. This size allows multiple serpentine back and forth loops of a light guide 982 to be arranged and secured across one surface of the pad 980 to supply light therapy over a wide area or over substantially the entire surface of the pad 980. The two ends 987 and 988 of the light guide 982 are connected to a single housing 990. One or two lasers may be mounted in the housing 990, as described above, for supplying laser light to one or both ends 987 and 988 of the light guide 982.

The light therapy apparatus can also be employed as an optical bandage. The optical bandage may have any suitable dimensions and shape, with either a square, rectangular, or polygonal or circular configuration being used depending upon the application. For example, the optical bandage can be one inch wide by two inches long and can have a multi-layer configuration, similar to that of the strips 820 or 960 described above. Multiple back and forth loops of the light tube provide light intensity over substantially the entire surface of the optical bandage. The ends of the light tube may be coupled to a single laser power and control housing as described in previous aspects of the light therapy apparatus.

It should also be noted that, as a feature of optical bandage 1010 shown in FIG. 24, the overall length of the optical bandage 1010 may be cut, as shown by dotted line 1018, to size the length of the bandage 1010 to meet the requirements of a particular application. The ends of each individual light tube or guide 1016, either in the original uncut length or after the overall length of the bandage 1010 has been cut as shown by dotted line 1018 can be sealed, capped or otherwise closed off to prevent the escape of light from the open ends of the light tubes 1016.

The optical bandage 1019 shown in FIG. 25 is similar except that the optical bandage 1019 includes four longitudinally extending light guides 1016 that are separate and discrete from each other. Each pair of light guides 1016 is optically coupled to a separate laser light source 1017 in FIG. 24 or in FIG. 25, and can be cut to length as at line 1020.

In any of the applications of a light tube, such as light tube 1016, the outer surface of the light tube 1016 can be abraded to form surface irregularities 1030, FIG. 26, along the entire length or for any partial length of the light tube 1016. The surface irregularities are in the form of nicks, scratches, grooves, depressions or other irregular shapes which typically have a short length and extend inward a short distance from the outer surface of the light tube 1016.

The surface irregularities 1030 form surfaces which deflect light passing through the interior of the light tube 1016 outwardly through the sides of the light tube 1016 thereby increasing the amount and intensity of side-scattered light from the light tube 1016.

The abrasion process can be any suitable abrasion process, such as grinding, sanding, laser etching, etc.

Figure 29:
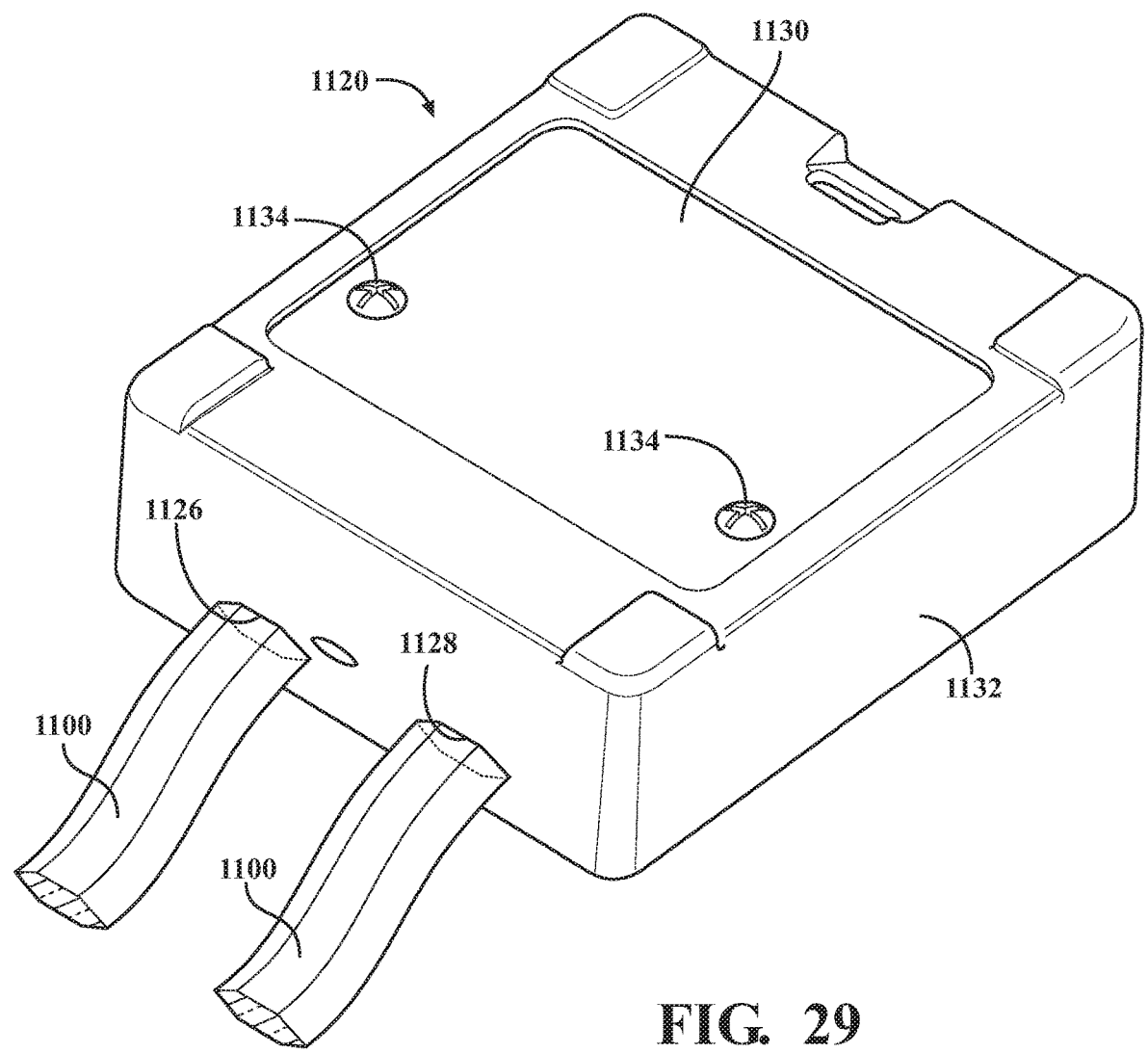
FIG. 29 is a perspective view of another aspect of a light therapy apparatus supporting dual optical light guides.

At the same time, the lead ends of the light tube 1016 may be removed from the apparatus 1120 in FIG. 29 and the apparatus 1120 slid from an enclosure on the optical bandage 1010, 1019 without disturbing the optical bandage 1010, 1019 covering the patient's wound. The apparatus 1120 may then be recharged and reinserted or a new apparatus 1120 inserted in the enclosure to continue light therapy applications.

Figure 27:
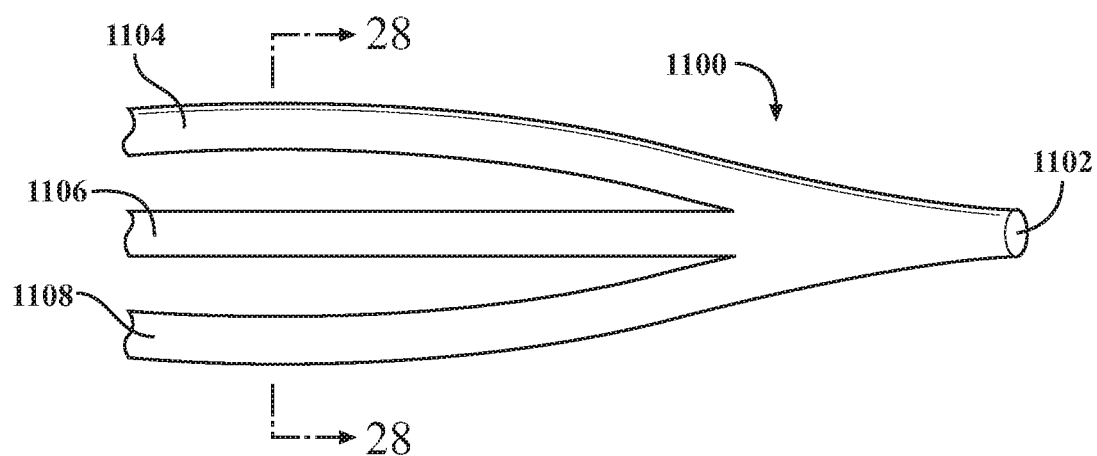
FIG. 27 is an elevational view of another aspect of a light guide with split light guide portions.
Figure 28:
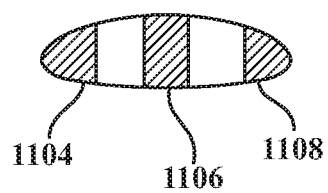
FIG. 28 is a cross sectional view generally taken along the line 28-28 in FIG. 27.

As shown in FIGS. 27 and 28, any of the light guides described above, and, in particular, the oval cross section light guide 1100 in FIG. 27, can be split into two or more separate, discrete light guide portions, with three separate light guide portions 1104, 1106 and 1108 shown by example in FIG. 27. The light guide 1100 includes a common, single end 1102. The split of the single light guide 1100 into the plurality of portions 1104, 1106 and 1108, etc., takes place a short distance from the single end 1102. This allows the end 1102 of the light guide 1100 to be optically coupled to the laser light source as a single end, rather than as a plurality of discrete ends.

Figure 30:
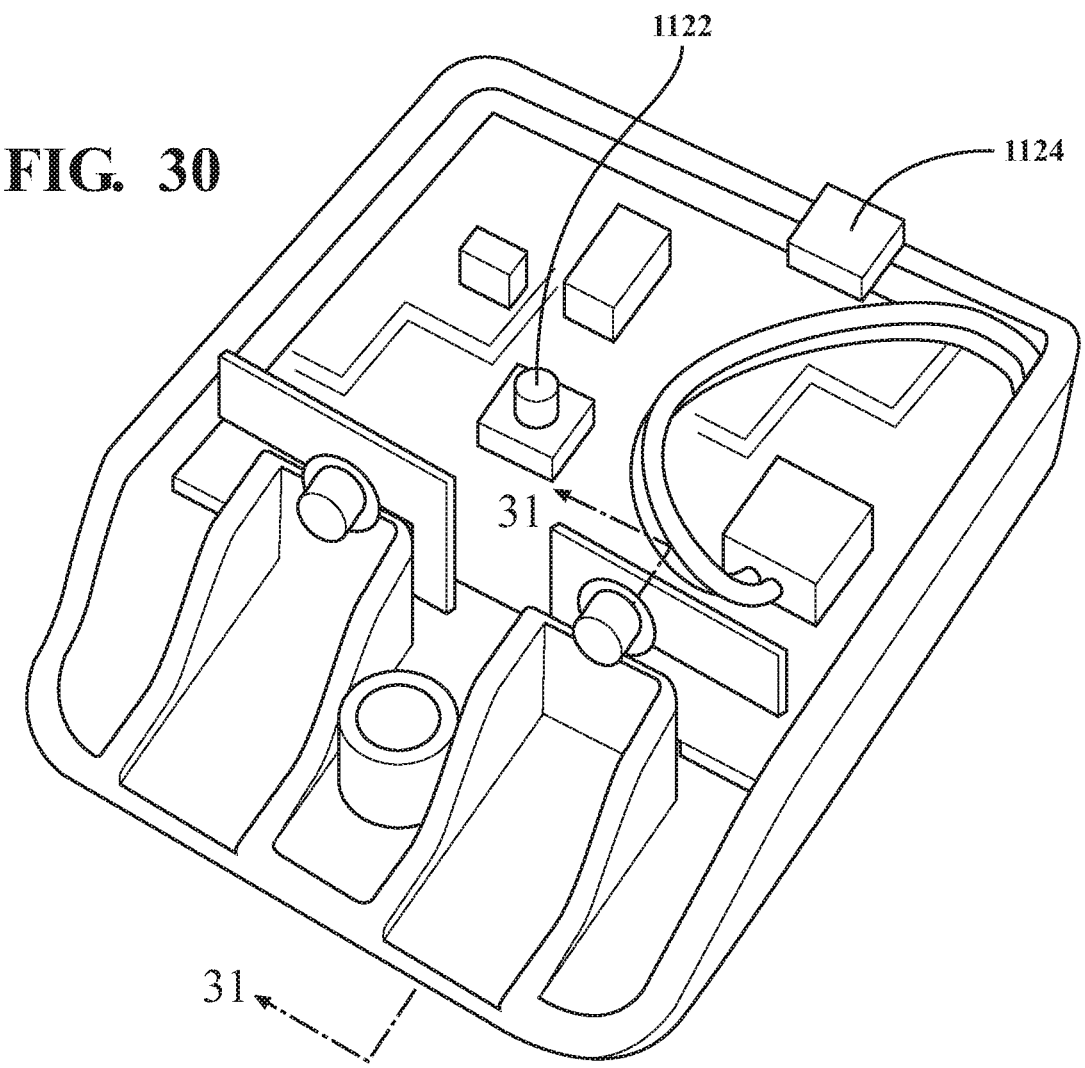
FIG. 30 is a perspective view of the bottom portion of the housing shown in FIG. 29.
Figure 31:
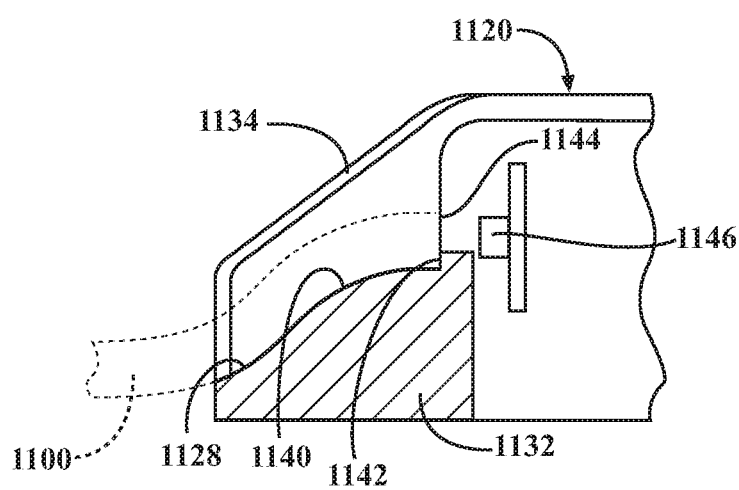
FIG. 31 is a cross sectional view generally taken along line 31-31 in FIG. 30.

FIGS. 29-31 depict another embodiment of a light therapy apparatus 1120 containing a power supply, a control circuit, an on-off switch 1122, a USB connector 1124, as well as one or more openings 1126 and 1128 for receiving individual light guides, such as light guide 1100, for example.

The apparatus 1120 includes a housing formed of two separable sections 1130 and 1132 that are joined together by fasteners 1134 extending through the joined housing sections 1130 and 1132.

As shown in detail in FIGS. 30 and 31, at least one ramp 1140 is formed at one end portion of the lowermost housing section 1132. The ramp 1140 extends from the opening 1128 at an upward angle to an opposed end 1142 which is at a higher elevation relative to the bottom of the housing section 1132 than the elevation of the bottom edge of the opening 1128. This offsets the end portion of the light guide 1100 extending through the opening 1128 from the opposed end 1144 of the light guide 1100 which is aligned with and optically coupled to the laser light source 1146 in the housing of the apparatus 1120. This enables a class I laser 1146 to be employed, while preventing light from the laser from being visible to the user if the user were to look through the opening 1128 in the housing when the light guide 1100 is separated from the housing.

Figure 32:
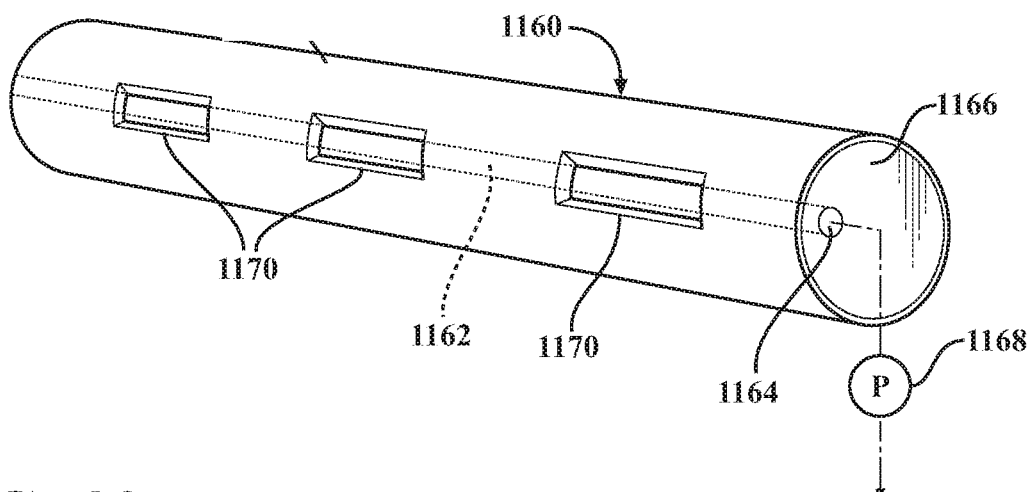
FIG. 32 is another aspect of a light guide usable with a vacuum suction pump device.

FIG. 32 depicts another modification to a light guide 1160, which may have any of the circular, oval or rectangular cross sections described above. The light guide 1160 includes a longitudinally extending bore 1162 positioned generally centrally along the longitudinal axis of the light guide 1160. The bore 1162 extends to an open end 1164 in one end 1166 of the light guide 1160. The open end 1164 in the bore 1162 may be coupled to a pump 1168 which forms part of a vacuum suctioning apparatus designed to suction exudate or fluids from open wounds through the light guide 1160. One or more openings or apertures 1170 is formed in the light guide 1160 at selected positions along the length of the light guide 1160. The openings 1170 communicate with the bore 1162 and provide a passage for allowing the vacuum pump 1168 to suction exudate through the openings 1170, into the bore 1162, and then through the bore 1162 and out of the open end 1164.

Figure 33:
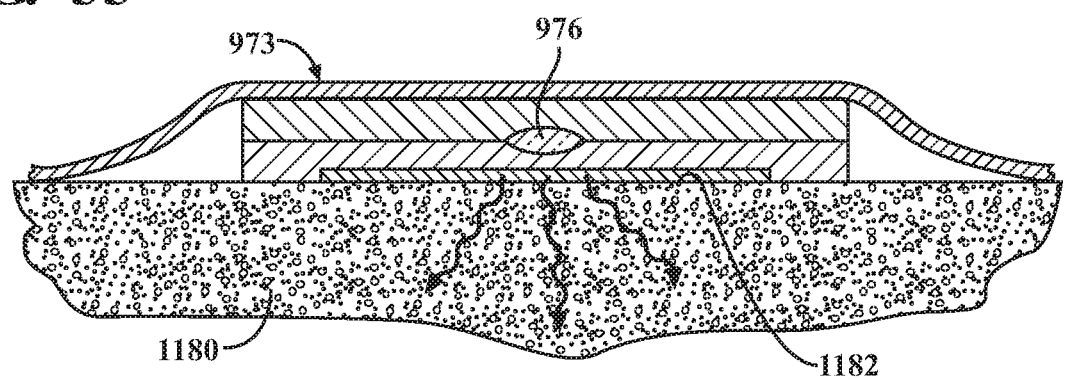
FIG. 33 is a cross sectional view showing one application of the light therapy apparatus.
Figure 34:
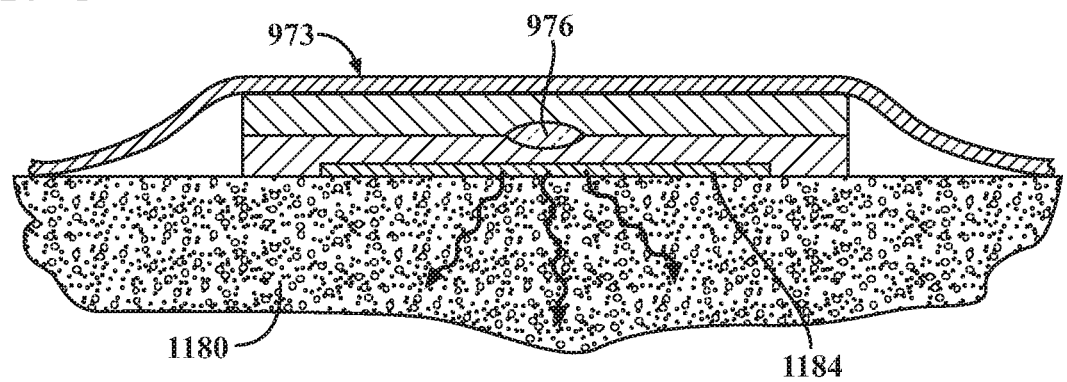
FIG. 34 is a cross sectional view showing another aspect of an application of the light therapy apparatus.

The light therapy apparatus, such as the pad or apparatus 973 shown in FIG. 19, may also be used to increase the penetration distance of medication, topical solutions, etc., into the user's skin tissue 1180 as shown in FIGS. 33 and 34. In FIG. 33, the light therapy apparatus 973 is secured to the user's skin 1180 over top of a thin layer of a medication, topical solution, etc., applied to the surface of the user's skin 1180.

In FIG. 34, the medication or topical solution is applied to a thin cotton pad 1184 which is then placed on the surface of the user's skin and covered by the light therapy apparatus 973.

In both applications, light from the light guide 976 will penetrate through the layer of medication or topical solution and drive the medication or topical solution further into the layers of the user's skin.

When the topical solution 1182 is applied directly to the skin 1180 or whether the medication or solution is pre-applied to the pad 1184, if the compound is hyaluronic acid, unexpected benefits are obtained by the use of the light therapy apparatus 973. It is believed that the light generated by the light therapy apparatus 973 causes cross linking of the smaller hyaluronic molecules in the various skin layers into larger molecules extending across the skin layers to firmly bind the skin together. This is particularly beneficial in post-surgery applications.

Most aspects of the light therapy apparatus described above may be employed as wearable light therapy apparatus. In a simple configuration, the wearable laser light therapy apparatus may include a pack or housing containing at least one laser light source, an onboard power supply storage battery or a connection to an external conductor and power supply, and a short length light guide which can be applied in any configuration, such as a back and forth serpentine configuration, a sinusoidal wave, or a plurality of spiral turns, etc., over a portion of the patient's body. For example, a 6 inch long light tube and single 5 mw lens-less laser can be used in the light therapy apparatus.

In addition to being wearable, the detachable or removably plugged in optical media or light tubes in the different laser therapy apparatus described above can be removed from the laser housing so that the pad or bandage in which the light tubes are mounted can be cleaned, disposed of and replaced with a new light tube and bandage. This increases the reliability of the laser means and the controls since the laser means and controls are not subject to exposure to water.

This arrangement is particularly advantageous for use with bandages which are replaced frequently when soiled.

What is claimed is:

1. A light therapy apparatus, comprising:
   a housing defining an interior space, including:
      an opening extending through a first surface of the housing from the interior space, the first surface perpendicular to a bottom of the housing;
   a laser mounted in the interior space and facing the first surface of the housing so as to output laser light towards the first surface;
   a control circuit mounted in the interior space that controls the laser according to a control program; and
   a power source mounted in the interior space and operatively coupled to the control circuit, wherein the housing and the laser are arranged so the laser light output from the laser is indirectly output through the opening, a bottom edge of the opening located at an elevation above the bottom of the housing and the laser facing the first surface of the housing at a higher elevation relative to the bottom of the housing than the elevation of the bottom edge of the opening such that a longitudinal axis of the laser light is offset from the opening.

2. The light therapy apparatus of claim 1, further comprising:
   a polymeric side scattering light guide having a first end facing the laser, and the polymeric side scattering light guide extending through the opening.

3. The light therapy apparatus of claim 1, wherein the housing further comprises a ramp extending from the opening at an upward angle to an opposed end at the higher elevation relative to the bottom of the housing than the elevation of the bottom edge of the opening.

4. The light therapy apparatus of claim 1, wherein the laser is a first laser, and the light therapy apparatus comprises a second laser mounted adjacent to the first laser at the higher elevation and facing the first surface.

5. The light therapy apparatus of claim 4, wherein the opening comprises a first opening, the light therapy apparatus further comprising a second opening adjacent to the second opening.

6. The light therapy apparatus of claim 5, further comprising:
   a polymeric side scattering light guide having a first end facing the first laser, and the polymeric side scattering light guide extending through the first opening and the second opening to a second end facing the second laser.

7. The light therapy apparatus of claim 1, wherein the laser is a class III laser or a class IV laser having an output power of at least 150 mW.

8. The light therapy apparatus of claim 1, wherein the control circuit controls a duty cycle for a laser diode of the laser for a time interval of application.

9. The light therapy apparatus of claim 8, wherein the time interval of application is 10 or 15 minutes.

10. The light therapy apparatus of claim 8, wherein the control circuit repeats the time interval of application for a selectable number of times over a longer time interval.

11. The light therapy apparatus of claim 1, further comprising:
    a user wearable carrier supporting the housing.

12. The light therapy apparatus of claim 1, further comprising:
    a light guide having a first end optically coupled to the laser and a plurality of individual light guides spaced extending away from the first end.

13. The light therapy apparatus of claim 1, further comprising:
    a light guide detachably coupled to the laser, the light guide scattering light along a length of the light guide.

14. The light therapy apparatus of claim 13, wherein the light guide has one of a circular cross section, an oval cross section, or an oval cross section with a side edge tapering to an edge.

15. The light therapy apparatus of claim 1, further comprising:
    a single light guide having one end optically coupled to the laser, the single light guide divided into a plurality of separate light guide portions joined together into a single light guide at the one end.

16. The light therapy apparatus of claim 15, wherein the separate light guide portions are joined into the single light guide at a location spaced from the one end of the single light guide.

17. The light therapy apparatus of claim 1, wherein the laser is a lens-less laser.

18. The light therapy apparatus of claim 1, wherein the housing comprises a single housing with an exterior shape corresponding to that of a rectangular prism, a USB connector is mounted on the housing, and the power source comprises a battery.

19. A light therapy apparatus, comprising:
    a housing, including:
       an opening extending through a first surface of the housing from an interior of the housing, the first surface perpendicular to a bottom of the housing;
    a laser mounted in the interior of the housing so as to output laser light towards the first surface of the housing; and
    a control circuit that controls the laser according to a control program, wherein the housing and the laser are arranged so the laser light output from the laser is indirectly output through the opening, and wherein the housing comprises two separable sections, the opening located between the two separable sections.

20. A light therapy apparatus, comprising:
    a housing, including:
       an opening extending through a first surface of the housing from an interior of the housing, the first surface perpendicular to a bottom of the housing;
    a laser mounted in the interior of the housing so as to output laser light towards the first surface of the housing; and
    a control circuit that controls the laser according to a control program, wherein the housing and the laser are arranged so the laser light output from the laser is indirectly output through the opening;
    a light guide mounted on a pad in a predetermined geometric arrangement; and
    first and second ends of the light guide disposed within the interior of the housing and in relation to the laser so as to simultaneously receive light from the laser for transmission of light simultaneously through both of the first and second ends along the light guide.

\* \* \* \* \*